United States Patent
Ueda et al.

(10) Patent No.: US 10,363,339 B2
(45) Date of Patent: Jul. 30, 2019

(54) WATER ABSORBENT AGENT COMPOSITION AND METHOD FOR PRODUCING SAME, AS WELL AS STORAGE AND STOCKING METHOD FOR SAME

(71) Applicant: NIPPON SHOKUBAI CO., LTD., Osaka (JP)

(72) Inventors: Manabu Ueda, Himeji (JP); Hiroyuki Ikeuchi, Himeji (JP); Yasuhisa Nakashima, Himeji (JP); Katsuyuki Wada, Himeji (JP)

(73) Assignee: NIPPON SHOKUBAI CO., LTD., Osaka-Shi, Osaka (JP)

( * ) Notice: Subject to any disclaimer, the term of this patent is extended or adjusted under 35 U.S.C. 154(b) by 0 days.

(21) Appl. No.: 14/357,916

(22) PCT Filed: Nov. 15, 2012

(86) PCT No.: PCT/JP2012/079660
§ 371 (c)(1),
(2) Date: May 13, 2014

(87) PCT Pub. No.: WO2013/073614
PCT Pub. Date: May 23, 2013

(65) Prior Publication Data
US 2014/0299815 A1    Oct. 9, 2014

(30) Foreign Application Priority Data

Nov. 15, 2011  (JP) ................. 2011-249291

(51) Int. Cl.
| | | |
|---|---|---|
| *A61F 13/53* | (2006.01) | |
| *A61L 15/26* | (2006.01) | |
| *A61L 15/40* | (2006.01) | |
| *A61L 15/46* | (2006.01) | |
| *A61L 15/60* | (2006.01) | |
| *B01J 20/22* | (2006.01) | |
| *B01J 20/26* | (2006.01) | |
| *B01J 20/28* | (2006.01) | |
| *B01J 20/30* | (2006.01) | |

(52) U.S. Cl.
CPC ............... *A61L 15/60* (2013.01); *A61L 15/26* (2013.01); *A61L 15/40* (2013.01); *A61L 15/46* (2013.01); *B01J 20/223* (2013.01); *B01J 20/267* (2013.01); *B01J 20/2805* (2013.01); *B01J 20/3085* (2013.01); *A61F 2013/530481* (2013.01); *A61F 2013/530708* (2013.01); *B01J 2220/44* (2013.01); *B01J 2220/485* (2013.01)

(58) Field of Classification Search
CPC ...................................................... B01J 20/261
See application file for complete search history.

(56) References Cited

U.S. PATENT DOCUMENTS

| | | |
|---|---|---|
| 5,980,879 A | 11/1999 | Hiroki et al. |
| 6,911,572 B1 | 6/2005 | Bruhn et al. |
| 2001/0053807 A1 | 12/2001 | Miyake et al. |
| 2003/0004479 A1 | 1/2003 | Ueda et al. |
| 2004/0048955 A1 | 3/2004 | Wada et al. |
| 2004/0110913 A1* | 6/2004 | Kanto ............... A61L 15/60 526/317.1 |
| 2004/0157989 A1 | 8/2004 | Bruhn et al. |
| 2005/0154133 A1 | 7/2005 | Engelhardt et al. |
| 2006/0263454 A1 | 11/2006 | Sugiyama et al. |
| 2007/0066167 A1 | 3/2007 | Wada et al. |
| 2007/0141338 A1 | 6/2007 | Ishizaki et al. |
| 2008/0234646 A1 | 9/2008 | Braig et al. |
| 2009/0012488 A1 | 1/2009 | Braig et al. |
| 2009/0036855 A1 | 2/2009 | Wada et al. |
| 2009/0208748 A1 | 8/2009 | Torii et al. |
| 2009/0298685 A1 | 12/2009 | Torii et al. |

(Continued)

FOREIGN PATENT DOCUMENTS

| | | |
|---|---|---|
| EP | 0 619 074 A1 | 10/1994 |
| EP | 1099474 | 5/2001 |

(Continued)

OTHER PUBLICATIONS

Supplemental European Search Report, dated Jul. 16, 2015, issued in EP Application No. 12849458.0, 7 pages.
International Search Report for PCT/JP2012/079660, dated Feb. 12, 2013.
Notification of Reasons for Refusal, dated May 12, 2015, from the Japanese Patent Office in corresponding JP Application No. 2013-544315, and English translation thereof.
International Preliminary Report on Patentability for PCT/JP2012/079660, dated May 30, 2014.
Japanese Office Action dated Jun. 7, 2016 that issued in a corresponding Patent Application No. 2013-544315, including English translation of the Japanese Office Action.
Kyoji Yoshino et al., Antioxidant Effects of Tea Catechins, J. Technology and Education, vol. 13, No. 1, 2016, pp. 1-7.

(Continued)

*Primary Examiner* — Peter F Godenschwager
(74) *Attorney, Agent, or Firm* — Dickinson Wright PLLC

(57) ABSTRACT

An object of the present invention is to provide (i) a water absorbent agent composition which has an excellent additional function (a deodorizing function in particular), which stably carries out the additional function even after being stored for a long term, and which is less stressful to skin when used as an absorbent article, (ii) a method for producing the water absorbent agent composition, and (iii) an absorbent core and an absorbent article. The water absorbent agent composition contains: a polycarboxylic acid (salt)-based water absorbent resin as a main component; a natural ingredient; and a temporal deterioration preventing agent. Further, a water absorbent agent composition is produced by simultaneously or separately mixing a natural ingredient and a temporal deterioration preventing agent with a water absorbent resin which is a crosslinked polymer of unsaturated monomers having carboxylic acid and/or a salt thereof.

14 Claims, No Drawings

(56) References Cited

U.S. PATENT DOCUMENTS

| | | |
|---|---|---|
| 2009/0321682 A1* | 12/2009 | Kajikawa ............... C08J 7/123 252/194 |
| 2010/0003209 A1 | 1/2010 | Braig et al. |
| 2010/0119830 A1 | 5/2010 | Braig et al. |
| 2010/0178513 A1 | 7/2010 | Braig et al. |
| 2010/0209379 A1 | 8/2010 | Furno et al. |
| 2010/0240808 A1 | 9/2010 | Wada et al. |
| 2010/0292078 A1 | 11/2010 | Braig et al. |
| 2011/0009272 A1 | 1/2011 | Wattebled et al. |
| 2011/0053767 A1 | 3/2011 | Braig et al. |
| 2012/0058074 A1 | 3/2012 | Braig et al. |
| 2012/0215190 A1 | 8/2012 | Kawashima |
| 2012/0305842 A1 | 12/2012 | Torii et al. |
| 2013/0037708 A1 | 2/2013 | Matsumoto et al. |

FOREIGN PATENT DOCUMENTS

| | | |
|---|---|---|
| EP | 2 208 756 A1 | 7/2010 |
| JP | 60-15886 | 8/1985 |
| JP | 60-158861 | 8/1985 |
| JP | 63-135501 | 6/1988 |
| JP | 2-41155 | 2/1990 |
| JP | 3-59075 | 3/1991 |
| JP | 4-139104 | 5/1992 |
| JP | 5-179053 | 7/1993 |
| JP | 7-310 | 1/1995 |
| JP | 7-165981 | 6/1995 |
| JP | 8-176338 | 7/1996 |
| JP | 9-75723 | 3/1997 |
| JP | 9-208787 | 8/1997 |
| JP | 10-66866 | 3/1998 |
| JP | 11-116829 | 4/1999 |
| JP | 11-241030 | 9/1999 |
| JP | 11-315148 | 11/1999 |
| JP | 2000-51339 | 2/2000 |
| JP | 2000-79159 | 3/2000 |
| JP | 2001-172124 | 6/2001 |
| JP | 2001-234087 | 8/2001 |
| JP | 2002-285021 | 10/2002 |
| JP | 2005-15482 | 1/2005 |
| JP | 2006-55833 | 3/2006 |
| JP | 2006-68731 | 3/2006 |
| JP | 2006-101714 | 4/2006 |
| JP | 2006-188436 A | 7/2006 |
| JP | 2007-61083 | 3/2007 |
| JP | 2009-207504 | 9/2009 |
| JP | 2009-531158 | 9/2009 |
| JP | 2010-131537 | 6/2010 |
| JP | 2011-092246 | 5/2011 |
| JP | 2012-170482 | 9/2012 |
| WO | 99/64485 | 12/1999 |
| WO | 2003/076514 | 9/2003 |
| WO | 2007/011058 | 1/2007 |
| WO | 2007/012581 | 2/2007 |
| WO | 2007/085531 | 8/2007 |
| WO | 2007/104641 | 9/2007 |
| WO | 2007/121940 | 11/2007 |
| WO | 2009/034154 | 3/2009 |
| WO | 2009/040106 | 4/2009 |
| WO | 2009/048145 | 4/2009 |
| WO | 2009/101060 | 8/2009 |
| WO | 2009/109524 | 9/2009 |
| WO | WO 2010/011020 A1 | 1/2010 |
| WO | 2010/052182 | 5/2010 |
| WO | 2010/079075 | 7/2010 |
| WO | 2010/130666 | 11/2010 |
| WO | 2010/130667 | 11/2010 |
| WO | 2011/023560 | 3/2011 |
| WO | 2011/023647 | 3/2011 |
| WO | 2011/136238 | 11/2011 |

OTHER PUBLICATIONS

Akira Murata et al., Bactericidal Action of Iron(II) and Mechanism of the Action, Bull. Fac. Agr., Saga Univ., 93: : 141-155 (2008), Laboratory of Applied Microbiology, pp. 141-155.

* cited by examiner

WATER ABSORBENT AGENT COMPOSITION AND METHOD FOR PRODUCING SAME, AS WELL AS STORAGE AND STOCKING METHOD FOR SAME

TECHNICAL FIELD

The present invention relates to a water absorbent agent composition and a method for producing the water absorbent agent composition, as well as a method for storing and stocking the water absorbent agent composition. To be more specific, the present invention relates to: a water absorbent agent composition which is applicable to sanitary goods such as paper diapers, sanitary napkins, and incontinence pads as a constituent thereof being less stressful to skin and having a stable deodorizing performance even after a long-term storage; a method for producing the water absorbent agent composition; as well as a method for storing and stocking the water absorbent agent composition.

BACKGROUND ART

A water absorbent resin is widely used as one of constituents (a main constituent) of sanitary goods (absorbent article) such as paper diapers, particularly paper diapers for aged adults, sanitary napkins, and incontinence pads, in order to absorb body fluids (urine or blood).

Such a water absorbent resin is required to have not only water absorbent performance such as a water absorption capacity (without load) (an amount of a liquid which can be absorbed and held by a water absorbent resin or water absorbent agent composition; a water absorbing capacity), a water absorption capacity under load, a water absorbent speed, and permeability, but also an additional function such as a deodorizing property, an antibacterial property, a low-coloring property, and prevention of a deterioration. So far, addition of compounds such as deodorants, antibacterial agents, aromatic substances, and coloring preventing agents to a water absorbent resin has been discussed.

For example, a water absorbent resin having a deodorizing function or antibacterial function is disclosed in Patent Literatures 1 to 29, 32, 33 etc., a water absorbent resin having an aromatic property is disclosed in Patent Literature 30 etc., and a water absorbent resin having a coloring preventing function is disclosed in Patent Literature 31.

Specifically, the aforementioned patent literatures disclose deodorants and combinations of deodorants and antibacterial agents in order to provide a water absorbent resin with a deodorizing function or antibacterial function. For example, the aforementioned patent literatures disclose a water absorbent agent composition of an essence extracted from leaves of Theaceae plants and a water absorbent resin (Patent Literature 1), a water absorbent agent composition of an essence extracted from conifers and a water absorbent resin having a specific performance (e.g. discontinuous absorption capacity under load performance) (Patent Literature 2), a water absorbent agent composition in which zeolite powder is dispersed inside a water absorbent resin (Patent Literature 3), a long-acting antibacterial deodorant containing a Japanese horse-radish extract, a mustard extract or the like, a maintaining agent (absorbent gelatinizer) for maintaining an antibacterial and deodorizing effect, and a water absorbent resin (Patent Literature 4), a deodorant and antibacterial water absorbing agent (composition) containing a compound having an antibacterial function against ammonia-producing bacteria etc. and a water absorbent resin (Patent Literature 5), and a water absorbent resin composition of an aminoacetic acid chelating agent and a water absorbent resin (Patent Literature 6).

Furthermore, as an attempt to provide absorbent articles using a water absorbent resin with a deodorizing function or an antibacterial function, the patent literatures disclose an absorbent article containing manufactured tea and a water absorbent resin (Patent Literature 7) and a disposable diaper containing a water absorbent resin containing benzalkonium chloride and/or chlorhexidine gluconate (Patent Literature 8).

Furthermore, in addition to the above water absorbent resin, as a water absorbent resin (water absorbent agent composition) provided with the deodorizing function or the antibacterial function, the patent literatures disclose a gelatinous insecticide prepared by causing a water absorbent resin to absorb a volatile monoterpene compound (Patent Literature 9), a method for producing a water absorbent resin composition in which an antibacterial membrane is formed on a surface of a water absorbent resin (Patent Literature 10), a water absorbent resin composition containing antibacterial phosphate (Patent Literatures 11 and 12), a water absorbent agent composition containing tannic acid (salt) and complex silicate compound (Patent Literature 13), a water absorbent agent composition containing a natural antibacterial ingredient extracted from grapefruit seeds and/or herbs (Patent Literature 14), a particulate water absorbent agent composition containing plant powder whose deodorizing index is not less than 180 (Patent Literature 15), a water absorbent agent composition obtained by covalent-bonding and/or ion-bonding cyclodextrin and/or cyclodextrin derivative (Patent Literature 16), a copolymer obtained by copolymerizing C2-C8 olefin or styrene and an acid anhydride (Patent Literature 17), a water absorbent resin composition containing keto acid (Patent Literature 18), a water absorbent resin composition containing thiophosphoric triamide substituted by C1-C30 alkyl group (Patent Literature 19), a water absorbent resin composition containing an urease inhibitor (Patent Literature 20), a water absorbent resin composition containing specific plants such as a ginkgo, willow, and meadow sweet (Patent Literature 21), a water absorbent resin composition containing hydrolyzable tannin (Patent Literature 22), a water absorbent resin composition containing oxidase (Patent Literature 23), a water absorbent resin composition containing 0.001 wt % of a chelating agent and 0.001-5 wt % A of tannin (Patent Literature 24), a water absorbent resin coated with triclosan (Patent Literature 25), a water absorbent resin composition containing metal oxide and metal peroxide (Patent Literature 26), a process for producing a superabsorbent, in which an anti-microbial agent and polyol are added concurrently with or immediately after surface-treating the superabsorbent (Patent Literature 27), a method for producing water-absorbing polymer particles, in which an amount of iron is controlled to be small and a chelating agent is added to a surface of a water absorbent resin (Patent Literature 28), a water absorbent resin composition in which dry-distilled essences of bamboo and green tea are blended with a water absorbent resin and which is disclosed as a water absorbent resin that is highly safe and has an antibacterial (bacteriostatic) function and a deodorizing function (Patent Literature 29), a water absorbent resin composition containing tannin whose molecular weight is not less than 1,000 (Patent Literature 32), and a water absorbent resin composition containing zinc salicylate (Patent Literature 33).

Furthermore, as a water absorbent resin having an aromatic property, the patent literatures specifically disclose a water absorbent resin containing at least one substance selected from cyclodextrin having a fragrant material, dextrin derivative, C6-C10 unsaturated aliphatic aldehyde, and C6-C10 unsaturated aliphatic alcohol and a polycarboxylic acid water absorbent resin (Patent Literature 30). Furthermore, as a water absorbent resin provided with a coloring inhibiting function, there is disclosed a water absorbent resin whose L value in a Lab color system is not more than 90 (Patent Literature 31).

Other than the water absorbent resins disclosed in the aforementioned patent literatures, there are proposed many water absorbent resins containing compounds each of which gives an additional function such as a deodorant, an antibacterial agent, an aromatic agent, a coloring preventing agent, and a deterioration inhibitor. Among them, the water absorbent resins using natural ingredients as disclosed in Patent Literatures 1, 2, 4, 7, 13-15, 21-24, 29 etc. are preferably used due to their high safeness. In the steps of producing such water absorbent resins, qualities thereof are exactly managed, and only water absorbent resins whose physical properties (water absorbent performance and the aforementioned additional function) satisfy predetermined standards (so-called acceptable products) are sold.

The inventors of the present invention have found that a water absorbent resin which contains a natural ingredient and to which an additional function, a deodorizing function in particular, is given decreases the additional function with time after the water absorbent resin is sold with its targeted quality satisfied. That is, the inventors of the present invention have found that since the additional function decreases with time after the water absorbent resin is produced, a period during which the water absorbent resin can be stored or stocked, i.e. a period during which a quality of the additional function given to the water absorbent resin is assured becomes shorter. Furthermore, the inventors of the present invention have found a problem such that in actual use of the water absorbent resin, the additional function cannot be carried out sufficiently.

On the other hand, although some documents of the conventional techniques, including the Patent Literatures 1 to 33, disclose a water absorbent resin to which an additional function (deodorizing function in particular) are given, none of those documents mentions a decrease in additional function with time, and therefore does not disclose use of a temporal deterioration preventing agent in the present invention.

CITATION LIST

Patent Literatures

[Patent Literature 1]
  Japanese Patent Application Publication, Tokukaisho, No. 60-158861 (1985)
[Patent Literature 2]
  Japanese Patent Application Publication, Tokukaihei, No. 11-241030 (1999)
[Patent Literature 3]
  Japanese Patent Application Publication, Tokukaihei, No. 8-176338 (1996)
[Patent Literature 4]
  Japanese Patent Application Publication, Tokukai, No. 2000-51339
[Patent Literature 5]
  Japanese Patent Application Publication, Tokukai, No. 2000-79159
[Patent Literature 6]
  Japanese Patent Application Publication, Tokukai, No. 2001-234087
[Patent Literature 7]
  Japanese Patent Application Publication, Tokukaihei, No. 2-41155 (1990)
[Patent Literature 8]
  Japanese Patent Application Publication, Tokukaisho, No. 63-135501 (1988)
[Patent Literature 9]
  Japanese Patent Application Publication, Tokukaihei, No. 4-139104 (1992)
[Patent Literature 10]
  Japanese Patent Application Publication, Tokukaihei, No. 3-59075 (1991)
[Patent Literature 11]
  Japanese Patent Application Publication, Tokukaihei, No. 5-179053 (1993)
[Patent Literature 12]
  Japanese Patent Application Publication, Tokukaihei, No. 7-165981 (1995)
[Patent Literature 13]
  Japanese Patent Application Publication, Tokukaihei, No. 11-116829 (1999)
[Patent Literature 14]
  Japanese Patent Application Publication, Tokukaihei, No. 9-208787 (1997)
[Patent Literature 15]
  Japanese Patent Application Publication, Tokukai, No. 2002-285021
[Patent Literature 16]
  International Publication No. WO99/64485, pamphlet
[Patent Literature 17]
  International Publication No. WO2003/076514, pamphlet
[Patent Literature 18]
  International Publication No. WO2007/104641, pamphlet
[Patent Literature 19]
  International Publication No. WO2007/012581, pamphlet
[Patent Literature 20]
  International Publication No. WO2007/085531, pamphlet
[Patent Literature 21]
  International Publication No. WO2009/101060, pamphlet
[Patent Literature 22]
  International Publication No. WO2010/052182, pamphlet
[Patent Literature 23]
  International Publication No. WO2010/130666, pamphlet
[Patent Literature 24]
  International Publication No. WO2010/130667, pamphlet
[Patent Literature 25]
  International Publication No. WO2011/023647, pamphlet
[Patent Literature 26]
  International Publication No. WO2011/023560, pamphlet
[Patent Literature 27]
  International Publication No. WO2009/034154, pamphlet
[Patent Literature 28]
  International Publication No. WO2010/079075, pamphlet
[Patent Literature 29]
  International Publication No. WO2009/048145, pamphlet
[Patent Literature 30]
  International Publication No. WO2007/011058, pamphlet
[Patent Literature 31]
  International Publication No. WO2007/121940, pamphlet
[Patent Literature 32]
  International Publication No. WO2009/040106, pamphlet

[Patent Literature 33]
International Publication No. WO2009/109524, pamphlet

SUMMARY OF INVENTION

Technical Problem

As described above, the inventors of the present invention have found a problem such that although basic water absorbent properties (water absorption capacity/water absorption capacity under load/permeability etc.) other than color hue of a water absorbent resin are approximately constant after being stored for a long term of several months to several years, the water absorbent resin decreases its additional function with time, and particularly a water absorbent resin to which an additional function (particularly deodorizing function) is given by using a natural ingredient decreases the additional function with time.

Therefore, a main object of the present invention is to provide a water absorbent agent composition which has an excellent additional function (a deodorizing function in particular) and basic water absorbent properties, which stably carries out the additional function even after being stored for a long term, and which is less stressful to skin when used as an absorbent article. Furthermore, another object of the present invention is to provide a method for producing a water absorbent agent composition having the above features, and an absorbent core and an absorbent article (article containing water absorbent agent composition) each of which uses the water absorbent agent composition. Still another object of the present invention is to provide a method for storing and stocking the water absorbent agent composition as a long-term stock.

Solution to Problem

The inventors of the present invention conducted a diligent study so as to attain the object, and finally found that in the case of a conventional water absorbent resin having an additional function (a deodorizing function in particular), the additional function was decreased over time by combining the water absorbent resin with a natural ingredient (natural deodorizing ingredient in particular) which was frequently used to provide the additional function, and particularly that the combination of the natural ingredient with the water absorbent resin more rapidly decreased the additional function than use of the natural ingredient alone. From this finding, the inventors of the present invention found that the object was attained by adding a small amount of a temporal deterioration preventing agent to the water absorbent resin containing the natural ingredient, which was combined with the water absorbent resin.

In order to attain the object, a water absorbent agent composition in accordance with the present invention contains: a polycarboxylic acid (salt)-based water absorbent resin as a main component; a natural ingredient; and a temporal deterioration preventing agent.

In order to attain the object, a method in accordance with the present invention for producing a water absorbent agent composition, includes: simultaneously or separately mixing a natural ingredient and a temporal deterioration preventing agent with a water absorbent resin which is a crosslinked polymer of unsaturated monomers having carboxylic acid and/or a salt thereof.

In order to attain the object, a water absorbent agent composition in accordance with the present invention is obtainable by a method mentioned above for producing a water absorbent agent composition.

In order to attain the object, a water absorbent agent package in accordance with the present invention includes a sealed container filled with a water absorbent agent composition mentioned above.

In order to attain the object, a water absorbent agent composition storing or stocking method in accordance with the present invention includes storing a water absorbent agent package mentioned above in a packaged state for not less than 30 days until the water absorbent agent package is actually used.

In order to attain the object, a packaged absorbent article for urine absorption in accordance with the present invention, contains a water absorbent agent composition mentioned above.

In order to attain the object, an absorbent article production method in accordance with the present invention includes producing an absorbent article for urine absorption by using a water absorbent agent composition containing: a packaged water absorbent resin as a main component; and a natural ingredient, the water absorbent agent composition further containing a temporal deterioration preventing agent.

Advantageous Effects of Invention

A water absorbent agent composition in accordance with the present invention contains: a polycarboxylic acid (salt)-based water absorbent resin as a main component; a natural ingredient; and a temporal deterioration preventing agent, the polycarboxylic acid (salt)-based water absorbent resin being, for example, a crosslinked polymer of unsaturated monomers having an acid radical and/or a salt thereof. An absorbent core of the present invention contains the water absorbent agent composition in accordance with the present invention, and is preferably used as, for example, an absorbing layer of an absorbent article such as a sanitary material. For example, an absorbent article in accordance with the present invention includes an absorbent core (absorbing layer) containing the water absorbent agent composition, a top sheet having liquid permeability, and a back sheet having liquid impermeability.

The water absorbent agent composition in accordance with the present invention allows an absorbent article to have an additional function (a deodorizing function in particular). The water absorbent agent composition is a novel water absorbent agent composition which continues to have an excellent additional function (a deodorizing function in particular) even after being stored for a long term.

An absorbent core and an absorbent article of the present invention each contain the water absorbent agent composition so as to have an excellent additional function (a deodorizing function in particular) of the water absorbent agent composition. Therefore, the absorbent core and the absorbent article are each particularly preferably used for sanitary materials such as a paper diaper, a sanitary napkin, an adult incontinence pad, and an adult paper diaper.

Therefore, according to the configurations, it is possible to yield an effect of providing a water absorbent agent composition in accordance with the present invention which water absorbent agent composition, when used (incorporated) in an absorbent article such as a paper diaper, is highly safe, has an excellent additional function (a deodorizing effect in particular), and can have the excellent additional function (the deodorizing effect in particular) even after being stored for a long term; a method for producing the water absorbent agent composition in accordance with the present invention; and an absorbent core and an absorbent article each containing the water absorbent agent composition in accordance with the present invention (each made of the water absorbent agent composition).

DESCRIPTION OF EMBODIMENTS

The following description will discuss in details a water absorbent agent composition in accordance with the present invention, a method of the present invention for producing the water absorbent agent composition, and a storage and stocking method of the present invention for the water absorbent agent composition. The scope of the present invention is not restricted by the description, and the present invention may be appropriately modified or carried out in a manner other than examples described below, as long as the spirit of the present invention is not impaired. Specifically, the present invention is not limited to the description of the embodiments below, but may be altered by a skilled person within the scope of the claims. An embodiment based on a proper combination of technical means disclosed in different embodiments is encompassed in the technical scope of the present invention.

[1] Definition of Terms (1-1) "Water Absorbent Resin"

A "water absorbent resin" as used in the present invention means a water-swelling, water-insoluble gelatinizer in the form of a polymer. It should be noted here that the "water-swelling" means that a CRC (water absorption capacity without load) specified in ERT 441.2-02 is not less than 5 [g/g], and the "water-insoluble" means that an Ext (water soluble component) specified in ERT 470.2-02 is not more than 50 wt %.

The water absorbent resin can be designed as appropriate depending on its use, and therefore is not particularly limited in its design. Note, however, that the water absorbent resin is preferably a hydrophilic crosslinked polymer obtained by polymerizing crosslinking unsaturated monomers each having a carboxyl group. Further, the water absorbent resin may be a water absorbent resin composition containing an additive (e.g. surfactant) etc., provided that the foregoing CRC and Ext are satisfied. Furthermore, the water absorbent resin may be surface-crosslinked one or non-surface-crosslinked one, and is not particularly limited in its shape, and may be sheet-like, fiber-like, powder-like, film-like, gelatinous or the like. These water absorbent resins, including the above water absorbent resin composition, are collectively referred to as "water absorbent resin".

Further, in the present invention, for convenience, a water absorbent resin having not yet been surface-crosslinked is referred to as a "water absorbent resin powder", and a water absorbent resin which has been surface-crosslinked is referred to as "water absorbent resin particles".

(1-2) "Polyacrylic Acid (Salt)"

As used in the present invention, the term "polyacrylic acid (salt)" means a polymer that optionally has a graft component and contains, as main components, repeating units constituted by an acrylic acid and/or a salt thereof (hereinafter referred to as acrylic acid (salt)). Specifically, the "polyacrylic acid (salt)" as used in the present invention means a polymer that contains, as monomers other than a crosslinking agent, acrylic acids (salts) in an amount between 30 mol % and 100 mol %.

(1-3) "Water Absorbent Agent Composition"

"Water absorbent agent composition" of the present invention indicates a water absorbent resin composition whose main component is the aforementioned water absorbent resin and which contains a natural ingredient capable of giving an additional function below and a temporal deterioration preventing agent. The water absorbent resin is preferably surface-crosslinked water absorbent resin particles. "Main component" as used herein indicates that the water absorbent resin or the water absorbent resin particles (solid content) is contained in a range preferably of not less than 50 wt % and less than 100 wt %, more preferably of 60 to 99.9 wt %, still more preferably of 70 to 99 wt %, and particularly preferably of to 98.9 wt % relative to the water absorbent agent composition.

(1-4) "EDANA" and "ERT"

The term "EDANA" stands for European Disposables and Nonwovens Associations. The term "ERT" stands for EDANA Recommended Test Methods, which is the European-standard (actually, the world-standard) method of measuring water absorbent resins.

Although the ERT is a method for measuring physical properties of a water absorbent resin, in the present invention, unless otherwise noted, the measurements of physical properties of the water absorbent agent composition are carried out in conformity with the original ERT (known document: revised in 2002). In the following description, physical properties of the water absorbent agent composition are described.

(a) "CRC" (ERT 441.2-02)

The term "CRC" stands for a centrifuge retention capacity, and means water absorption capacity without load (hereinafter may be referred to as "water absorption capacity"). Specifically, the "CRC" is water absorption capacity (Unit: [g/g]) observed in 0.2 g of a water absorbent agent composition in an unwoven cloth when the water absorbent agent composition is allowed to freely swell in an excess amount of 0.9 wt % aqueous solution of sodium chloride without load for 30 min and thereafter is subjected to water spinning-off with use of a centrifugal machine.

(b) "AAP" (ERT 442.2-02)

The term "AAP" stands for absorption against pressure, and means water absorption capacity under load. Specifically, the "AAP" is water absorption capacity (Unit: [g/g]) observed in 0.9 g of a water absorbent agent composition after the water absorbent agent composition is allowed to swell in an excess amount of a 0.9 wt % aqueous solution of sodium chloride under a load of 2.06 kPa (0.3 psi) for 1 hour.

(c) "Ext" (ERT 470.2-02)

The term "Ext" stands for Extractables, and means a water soluble component (the amount of extractable components). Specifically, the "Ext" is a value (Unit: wt %) measured by pH titration to measure the amount of polymers dissolved in a solution obtained by adding 1.0 g of a water absorbent agent composition to 200 ml of a 0.9 wt % aqueous solution of sodium chloride and stirring the solution with a stir bar of 30 mm in length at 500 rpm for 16 hours.

(d) "Residual Monomers" (ERT410.2-02)

The term "residual monomers" means an amount of monomers remaining in a water absorbent agent composition. Specifically, "residual monomers" means a value (Unit: ppm) obtained by high-performance liquid chromatography to measure the amount of residual monomers dissolved in a solution prepared by adding 0.5 g of a water absorbent agent composition to 200 ml of a 0.9 wt % aqueous solution of sodium chloride and stirring the solution with a stir bar of 30 mm in length at 500 rpm for 2 hours.

(e) "PSD" (ERT 420.2-02)

The term "PSD" stands for particle size distribution, and means a particle size distribution measured by sieve classification. It should be noted that weight average particle diameter (D50), the particle diameter distribution, and a width thereof (logarithmic standard deviation σζ) are measured in the same manner as in the "(1) Average Particle Diameter and Distribution of Particle Diameter" described in European Patent No. 1594556.

(f) "SFC" and "GBP"

The term "SFC" stands for Saline Flow Conductivity. The term "GBP" stands for Gel Bed Permeability. "SFC" and "GBP" herein are representative ways for measuring "permeability" indicative of flowability of a liquid flowing through particles of swollen gels under load or without load.

"SFC (Saline Flow Conductivity)" means permeability of a 0.69 wt % aqueous solution of sodium chloride in a water absorbent resin under load of 2.07 kPa, and is measured in accordance with a SFC test method disclosed in U.S. Pat. No. 5,669,894. "GBP" means permeability of a 0.69 wt % aqueous solution of sodium chloride in a water absorbent resin under load or a freely swollen water absorbent resin, and is measured in accordance with a GBP test method disclosed in WO2005/016393.

(1-5) Other

In this Description, the phrase "X to Y", which is indicative of a range, means that "not less than X but not more than Y". Further, the term "t (ton)", which is a unit of weight, means a "metric ton". Further, unless otherwise noted, the term "ppm" means "ppm by weight" or "ppm by mass". Further, "weight" and "mass" are treated as being synonymous, "wt %" and "mass %" are treated as being synonymous, and "part by weight" and "part by mass" are treated as being synonymous. Further, "acid (salt)" means "acid and/or salt thereof", and the term "meth(acryl)" means "acryl and/or methacryl".

[2] Method for Producing Water Absorbent Resin

The following description discusses a method for producing a water absorbent resin, preferably water absorbent resin particles for use as a main component of the water absorbent agent composition in accordance with the present invention.

(2-1) Polymerization Step

A polymerization step of the present invention is a step of obtaining a hydrous gelatinous crosslinking polymer (hereinafter referred to as a "hydrogel") by polymerizing acid radical-containing unsaturated monomers.

(Acid Radical-Containing Unsaturated Monomers (Excluding Crosslinking Agent))

From the viewpoint of a deodorizing effect and a water absorbent property, a water absorbent resin which has a crosslinked structure and is obtained by polymerizing acid radical-containing unsaturated monomers is essentially used in an embodiment of the present invention. Examples of such an acid radical-containing unsaturated monomer for use in the present invention include monomers (such as acrylonitrile) which become an acid radical by a hydrolysis after polymerization. However, a monomer which has an acid radical at polymerization is preferably used, and an unsaturated monomer which has carboxylic acid and/or a salt thereof is more preferably used.

Specific examples of a water absorbent resin which is obtained by polymerizing the acid radical-containing monomers include (partially) neutralized crosslinked polycarboxylic acid (salt) such as (partially) neutralized crosslinked polyacrylic acid, a hydrolyzed starch-acrylonitrile graft polymer, a neutralized starch-acrylic acid graft polymer, a saponified vinyl acetate-acrylic acid ester copolymer, crosslinked carboxymethylcellulose, a hydrolyzed acrylonitrile copolymer or acrylamide copolymer, or a crosslinked hydrolyzed acrylonitrile copolymer or acrylamide copolymer, a crosslinked cationic monomer, a carboxyl group-containing crosslinked polyvinyl denatured alcohol, a crosslinked isobutylene-maleic anhydride copolymer, and crosslinked 2-acrylamide-2-methylpropanesulfonic acid and acrylic acid, etc. Of these water absorbent resins, a polycarboxylic acid (salt)-based water absorbent resin, particularly (partially) neutralized crosslinked polyacrylic acid (also referred to as a "polyacrylic acid (salt)-based water absorbent resin") obtained by polymerizing monomers having acrylic acid and/or a salt thereof (neutralized product) as a main component is more preferable.

In a case where a water absorbent resin such as the polyacrylic acid (salt)-based water absorbent resin contains a neutralized acid radical, an acid radical has a neutralization rate (mol % of a neutralized acid radical relative to the total acid radical in a case where an acid radical contained in a water absorbent resin is 100 mol %) preferably of 10 to 100 mol %, more preferably of 20 to 90 mol %, still more preferably of 30 to 80 mol %, and particularly preferably of 40 to 80 mol %. By causing the neutralization rate to fall within the above range, it is possible to prevent a decrease in deodorizing effect of a water absorbent resin of the present invention.

(Graft Component and the Other Monomers)

In a case where the acid radical-containing unsaturated monomers each containing acrylic acid (salt) as a main component are used in an embodiment of the present invention, the acid radical-containing unsaturated monomers can each optionally contain a graft polymer component (e.g., water absorbent resin fine powder, polyvinyl alcohol, starch, cellulose, or the like) in an amount of 0 to 30 wt % relative to the acrylic acid (salt) as a main component.

Further, specific examples of the other monomers to be used in combination include water-soluble or hydrophobic unsaturated monomers such as methacrylic acid, (anhydrous) maleic acid, fumaric acid, crotonic acid, itaconic acid, vinylsulfonic acid, 2-(meth)acrylamide-2-methylpropanesulfonic acid, (meth)acryloxyalkane sulfonic acid and alkali metal salt or ammonium salt thereof, N-vinyl-2-pyrrolidone, N-vinylacetamide, (meth)acrylamide, N-isopropyl(meth)acrylamide, N,N-dimethyl(meth)acrylamide, 2-hydroxyethyl(meth)acrylate, methoxypolyethylene glycol (meth)acrylate, polyethylene glycol(meth)acrylate, isobutylene, and lauryl (meth)acrylate, and monomer compositions containing these monomers (copolymerization ingredients). It is preferable that a ratio of the other monomers to the acid radical-containing unsaturated monomers be 0 to 30 mol % relative to acrylic acid (salt) contained in the acid radical-containing unsaturated monomers as a main component (a ratio of the acrylic acid (salt) to the acid radical-containing unsaturated monomers be approximately not less than 77 mol %). It is more preferable that a ratio of the other monomers to the acid radical-containing unsaturated monomers be 0 to 10 mol % relative to acrylic acid (salt) contained in the acid radical-containing unsaturated monomers as a main component (a ratio of the acrylic acid (salt) to the acid radical-containing unsaturated monomers be approximately not less than 91 mol %).

(Internal Crosslinking Agent)

In an embodiment of the present invention, a crosslinked structure is essential to a water absorbent resin to be used. The crosslinked structure may be a self-crosslinking-type structure which is obtained by using no crosslinking agent; or a structure which is obtained by carrying out crosslinking by using a crosslinking agent (internal crosslinking agent) having, in one molecule, two or more polymerizable unsaturated groups or reactive groups, and is preferably a crosslinked structure which is obtained by carrying out crosslinking (copolymerization or a reaction) by using the internal crosslinking agent.

Specific examples of the internal crosslinking agent include N,N'-methylenebis(meth)acrylamide, (poly)ethylene glycol di(meth)acrylate, (poly)propylene glycol di(meth)acrylate, trimethylolpropane di(meth)acrylate, trimethylolpropane tri(meth)acrylate, glycerine tri(meth)acrylate, glycerine acrylate methacrylate, ethylene oxide denatured trimethylolpropane tri(meth)acrylate, pentaerythritol tetra(meth)acrylate, dipentaerythritol hexa(meth)acrylate, triallyl cyanurate, triallyl isocyanurate, triallyl phosphate, triallylamine, poly(meth)allyloxyalkane, (poly)ethylene glycol diglycidyl ether, glycerol diglycidyl ether, ethylene glycol, polyethylene glycol, propylene glycol, glycerine, pentaerythritol, ethylenediamine, ethylene carbonate, propylene carbonate, polyethyleneimine, glycidyl(meth)acrylate, and the like.

These internal crosslinking agents may be appropriately used alone or in combination of two or more kinds. From the viewpoint of, for example, a water absorbent property of a water absorbent agent composition to be finally obtained, it is preferable to use a crosslinking agent which contains two or more polymerizable unsaturated groups. Further, the internal crosslinking agent is used in an amount preferably of 0.001 to 2 mol %, more preferably of 0.005 to 0.5 mol %, still more preferably of 0.01 to 0.2 mol %, and particularly preferably of 0.03 to 0.15 mol %, relative to the acid radical-containing unsaturated monomers (excluding the crosslinking agent). In a case where the internal crosslinking agent is used in an amount falling within the above range, it is possible to provide the water absorbent resin of the present invention with a sufficient water absorbent property. Note that a degradable soluble component (described later) is reduced (to, for example, not more than 40%) by, for example, increasing the internal crosslinking agent in amount (to, for example, 0.1 mol %). Alternatively, the degradable soluble component may be reduced by using a water-soluble chain transfer agent at polymerization.

It is only necessary to add the internal crosslinking agent before or after neutralization of the acid radical-containing unsaturated monomers, or before, during, or after polymerization of the acid radical-containing unsaturated monomers. Further, one kind, or two or more kinds of the internal crosslinking agent(s) may be collectively or separately added. Note that whether or not the water absorbent resin of the present invention has a crosslinked structure can be determined by determining whether or not it is "water-swelling" or "water-insoluble" defined in the above (1-1).

(Polymerization Initiator)

A polymerization initiator for use in an embodiment of the present invention is appropriately selected in accordance with a form of polymerization. Therefore, such a polymerization initiator is not particularly limited. The polymerization initiator is exemplified by a photolytic polymerization initiator, a pyrolytic polymerization initiator, a redox polymerization initiator, and the like. From the viewpoint of a physical property (e.g., a water absorbent property), the polymerization initiator is used in an amount preferably of 0.0001 to 2 mol %, and more preferably of 0.01 to 0.1 mol %, relative to the acid radical-containing unsaturated monomers. In a case where the polymerization initiator is used in an amount falling within the above range, it is possible to reduce residual monomers while maintaining, at a high level, a water absorbent property of the water absorbent resin of the present invention as a water-swelling or water-insoluble polymer gelatinizer.

Note that examples of the photolytic polymerization initiator include a benzoin derivative, a benzyl derivative, an acetophenone derivative, a benzophenone derivative, an azo compound, and the like. Examples of the pyrolytic polymerization initiator include persulfates such as sodium persulfate, potassium persulfate, and ammonium persulfate; peroxides such as hydrogen peroxide, t-butyl peroxide, and methylethylketone peroxide; azo compounds such as 2,2'-azobis(2-amidino propane)dihydrochloride and 2,2'-azobis[2-(2-imidazoine-2-yl)propane]dihydrochloride; and the like. Further, the redox polymerization initiator is exemplified by a combination of a persulfate or a peroxide described above and a reducing compound such as L-ascorbic acid or sodium hydrogen sulfite. Use in combination of the photolytic polymerization initiator and the pyrolytic polymerization initiator may also be a preferable aspect of the present invention.

(Polymerization Method)

The water absorbent resin of the present invention can be obtained by carrying out bulk polymerization or precipitation polymerization of the acid radical-containing unsaturated monomers (hereinafter merely referred to as "monomers"). From the viewpoint of a water absorbent property, easiness of control of polymerization, and the like, it is preferable to carry out spray polymerization, drop polymerization, aqueous solution polymerization, or reverse phase suspension polymerization in which the monomers are in a form of an aqueous solution (hereinafter referred to as a "monomeric aqueous solution"). Of these polymerization methods, from the viewpoint of stability and productivity during production, and a water absorbent property (a water absorption capacity/a water absorption capacity under load), aqueous solution polymerization or reverse phase suspension polymerization is particularly preferable.

In a case the monomeric aqueous solution is used, a concentration (contained amount) of the monomers depends on a temperature of the monomeric aqueous solution or kinds of the monomers. Therefore, the concentration is not particularly limited. The monomeric aqueous solution contains the monomers in an amount preferably of 10 to 70 wt %, and more preferably of 20 to 60 wt %. The monomeric aqueous solution which contains the monomers in an amount falling within the above range allows an improvement in water absorbent property of the water absorbent resin of the present invention. In a case where the monomeric aqueous solution is polymerized, particularly in a case where aqueous solution polymerization is carried out, a solvent other than water may be used in combination according to need, and the solvent is not particularly limited in kind. Note that, as described later, from the viewpoint of prevention of coloring and prevention of a deterioration, a water absorbent agent composition preferably contains iron (Fe) in a smaller amount, and contains iron (Fe) in an amount falling within a range (described later) by, for example, controlling an amount of Fe contained in a base for use in neutralization. The acid radical-containing unsaturated monomers (per solid content) of the present invention contains iron (Fe) in an amount preferably of not more than 2 ppm, more preferably of not more than 1.5 ppm, still more preferably of not more than 1 ppm, and particularly preferably of not more than 0.5 ppm. In view of a cost and a polymerization speed, a lower limit of the amount of Fe is preferably 0.001 ppm, and more preferably 0.01 ppm.

Note that the aqueous solution polymerization is a method in which a monomer aqueous solution is polymerized without using any dispersion solvent. For example, the aqueous solution polymerization method is disclosed in U.S. patents such as U.S. Pat. Nos. 4,625,001, 4,873,299, 4,286,082, 4,973,632, 4,985,518, 5,124,416, 5,250,640, 5,264,495, 5,145,906, and 5,380,808; and European Patents such as European Patent No. 0811636, European Patent No. 0955086, and European Patent No. 0922717.

The reverse phase suspension polymerization is a polymerization method in which a monomer aqueous solution is suspended in a hydrophobic organic solvent. For example, the reverse phase suspension polymerization is disclosed in U.S. patents such as U.S. Pat. No. 4,093,776, 4,367,323, 4,446,261, 4,683,274, and 5,244,735. Note that monomers or polymerization initiators, methods for drying after polymerization, or the like described in the above U.S. patents or European Patents are also applicable to an embodiment of the present invention.

Such polymerization as described above can also be carried out in an air atmosphere. From the viewpoint of prevention of coloring, the polymerization is preferably carried out in an atmosphere of an inert gas such as nitrogen or argon (e.g., at an oxygen concentration of not more than 1 vol %). It is preferable that the polymerization be carried out after dissolved oxygen contained in the monomers or the monomeric aqueous solution is sufficiently substituted with the inert gas (for example, the oxygen concentration becomes less than 1 [mg/l]).

(2-2) Gel-Crushing Step

A gel-crushing step of the present invention is a step of obtaining a particulate hydrogel by shredding, according to need, a hydrogel obtained in the polymerization step. Note that polymerization of the monomers and shredding of the hydrogel may be simultaneously carried out depending on a form of polymerization (e.g., kneader polymerization or the like).

The hydrogel obtained in the polymerization step may be dried as it is. In the case of aqueous solution polymerization, it is preferable that the hydrogel be shredded by use of, for example, a gel-crusher (a kneader, a meat chopper, or the like) during or after the polymerization according to need, and then be dried.

In an embodiment of the present invention, the hydrogel is shredded by use of various methods, and how to shred the hydrogel is not particularly limited. For example, the hydrogel may be shredded by a method in which a screw-type extrusion machine that has a porous structure having any shape is used as a gel-crusher.

The particulate hydrogel has a weight average particle diameter preferably of 0.1 to 50 mm, more preferably of 0.2 to 10 mm, and still more preferably of 0.5 to 5 mm. The particulate hydrogel which has a weight average particle diameter falling within the above range allows an improvement in water absorbent property of the water absorbent resin or the water absorbent agent composition of the present invention.

(2-3) Drying Step

A drying step of the present invention is a step of obtaining a dried polymer by drying the particulate hydrogel (including the hydrogel). A method for carrying out the drying is exemplified by but not particularly limited to heat drying, hot-air drying, reduced-pressure drying, infrared drying, microwave drying, drum dryer drying, dehydration by azeotropy with a hydrophobic organic solvent, high humidity drying by use of high-temperature water vapor, and the like. Of these drying methods, from the viewpoint of productivity and a water absorbent property, hot-air drying or dehydration by azeotropy is preferable. Drying is carried out at a temperature falling within a range normally of 60 to 250° C., preferably of 100 to 220° C., and still more preferably of 120 to 200° C.

Drying time, which depends on a surface area and/or a moisture content of the particulate hydrogel, a kind of a dryer, and the like, is appropriately set so that a water absorbent agent composition to be obtained has a moisture content falling within an intended range. From the viewpoint of a color hue and a water absorbent property of a water absorbent resin or a water absorbent agent composition, drying time is preferably 10 seconds to 2 hours, more preferably 1 minute to 1.5 hour, and still more preferably 10 minutes to 1 hour.

Note that from the viewpoint of colorability, the particulate hydrogel discharged in the gel-crushing step is introduced into the drying step desirably in a shorter time, preferably within 2 hours, more preferably within 1 hour, still more preferably within 30 minutes, particularly preferably within 10 minutes, and most preferably within 2 minutes.

(2-4) Pulverizing Step

A pulverizing step of the present invention is a step of pulverizing, according to need, the dried polymer obtained in the drying step into particles having a size falling within a given range. A method for carrying out the pulverization is exemplified by but not particularly limited to a method for carrying out the pulverization by use of, for example, a vibration mill, a roll granulator, a knuckle-type pulverizer, a high-speed rotation-type pulverizer (a pin mill, a hammer mill, a screw mill, a roll mill, or the like), a cylindrical mixer, or the like.

(2-5) Classification Step

A classification step (first classification step) of the present invention is a step of obtaining water absorbent resin powder by sorting, into only particles having a given particle size, the dried polymer obtained after the drying step (and further pulverized in the pulverizing step according to need). A method for carrying out the classification is exemplified by but not particularly limited to sieve classification by use of a sieve. More specifically, assuming that water absorbent resin powder to be obtained has a particle diameter of 150 to 850 μm, after the pulverized dried polymer is sieved by use of a sieve having a mesh opening size of 850 μm, the dried polymer having passed through the mesh opening size of 850 μm is sieved by use of a sieve having a mesh opening size of 150 μm. This causes the dried polymer remaining on the sieve having a mesh opening size of 150 μm to be water absorbent resin powder having a particle diameter of 150 to 850 μm.

The water absorbent resin powder thus obtained, which has a large surface area per unit weight, not only increases a water absorbent speed but also easily carries out an additional function (a deodorizing function in particular). Note that a shape of particles of the water absorbent resin powder is exemplified by but not particularly limited to, for example, a spherical shape, a crushed shape, or an indefinite shape. From the viewpoint of a size of a surface area, a non-uniformly pulverized shape is preferable. Further, from the viewpoint of a physical property (e.g., a water absorbent property) of a water absorbent agent composition, the water absorbent resin powder has a bulk specific gravity (specified in JIS K-3362) preferably of 0.40 to 0.80 [g/ml], more preferably of 0.50 to 0.75 [g/ml], and still more preferably of 0.60 to 0.73 [g/ml].

The water absorbent resin powder has a moisture content (an amount of water contained in a water absorbent resin or a water absorbent agent composition; specified by a drying loss obtained when 1 g of a water absorbent resin or a water absorbent agent composition is dried at 180° C. for 3 hours) preferably of 0.2 to 30 wt %, more preferably of 0.3 to 15 wt %, and still more preferably of 0.5 to 10 wt %. This is because the water absorbent resin powder is required to exhibit flowability at a normal temperature (20 to 25° C., particularly 25° C.) from the viewpoint of a physical property (e.g., a water absorbent property) and handleability of a water absorbent agent composition to be obtained. The water absorbent resin powder which has a moisture content falling within the above range can have a higher impact resistance and maintain the additional function (the deodorizing function in particular) at a high level. Meanwhile, the water absorbent resin powder which has an excessively high moisture content causes not only a decrease in water absorbent performance but also accelerates decomposition of a natural ingredient, and may cause a temporal deterioration in additional function in some cases.

The water absorbent resin powder has a weight average particle diameter (D50) as a particle size preferably of 200 to 700 μm, more preferably of 300 to 600 μm, and still more preferably of 400 to 500 μm. The water absorbent resin powder contains particles having a particle diameter of not less than 150 μm and less than 850 μm in a ratio preferably of not less than 90 wt %, more preferably of not less than 95 wt %, and still more preferably of not less than 98 wt % (upper limit: 100 wt %). Further, the water absorbent resin powder contains particles having a particle diameter of not less than 300 μm in a ratio preferably of not less than 60 wt %, more preferably of not less than 65 wt %, still more preferably of not less than 70 wt %, and particularly preferably of not less than 75 wt %. The water absorbent resin powder which has a particle size falling within the above range allows an improvement in physical property (water absorption capacity under load and liquid permeability in particular) and further in moisture absorption blocking rate of the water absorbent resin of the present invention which water absorbent resin has been surface-crosslinked, so that a water absorbent resin composition which is suitable particularly to a sanitary material can be obtained.

Note that the above particle size is applied to water absorbent resin particles which have been surface-crosslinked, and further to a water absorbent agent composition as an end product. Therefore, it is preferable to carry out a surface-crosslinking treatment with respect to water absorbent resin particles so that the water absorbent resin particles which have been surface-crosslinked continues to have a particle size falling within the above range. Further, the particle size may be adjusted after the surface-crosslinking according to need by, for example, crushing of an agglomerate after the surface-crosslinking (operation of breaking up an agglomerated particle), classification (a second classification step), or granulation.

(2-6) Surface-Crosslinking Step

A surface-crosslinking step of the present invention is a step of providing a part having a higher crosslink density for a surface layer of water absorbent resin powder to be obtained through the steps described earlier (a part of the water absorbent resin powder which part extends from a surface of the water absorbent resin powder to a place located at a depth of several ten μm from the surface). The part having a higher crosslink density is formed by radical crosslinking or surface polymerization, a crosslinking reaction with a surface-crosslinking agent, or the like carried out on the surface of the water absorbent resin powder.

In an embodiment of the present invention, though it is possible to use, as a water absorbent resin for use in a water absorbent agent composition, water absorbent resin powder to be obtained through the polymerization step, the drying step, the pulverizing step, and the classification step, it is preferable to use water absorbent resin particles which have been surface-crosslinked (secondarily crosslinked). The water absorbent resin particles which have been surface-crosslinked (secondarily crosslinked) allow an increase in absorption against pressure (AAP) and liquid permeability (e.g., SFC and GBP). Therefore, for example, a water absorbent agent composition as a paper diaper not only improves in water absorbent performance but also improves in additional function (deodorizing function in particular) because a gap between particles of the water absorbent agent composition is maintained even after the water absorbent agent composition has been swollen.

A crosslinking agent (surface-crosslinking agent) for use in the surface-crosslinking step described earlier is exemplified by but not particularly limited to crosslinking agents mentioned in U.S. patents such as U.S. Pat. No. 5,409,771, 6,228,930, 6,071,976, and 6,254,990. More specific examples of the crosslinking agent include polyhydric alcohol compounds such as mono, di, tri, tetra, or polyethylene glycol, monopropylene glycol, 1,3-propanediol, dipropylene glycol, 2,3,4-trimethyl-1,3-pentanediol, polypropylene glycol, glycerine, polyglycerine, 2-butene-1,4-diol, 1,4-butanediol, 1,3-butanediol, 1,5-pentanediol, 1,6-hexanediol, and 1,2-cyclohexanedimethanol; epoxy compounds such as ethylene glycol diglycidyl ether and glycidol; polyvalent amine compounds such as ethylenediamine, diethylenetriamine, triethylenetetramine, tetraethylenepentamine, pentaethylenehexamine, polyethyleneimine, and polyamide polyamine; haloepoxy compounds such as epichlorohydrin, epibromhydrin, and α-methylepichlorohydrin; condensates of the polyvalent amine compounds and the haloepoxy compounds; oxazolidinone compounds such as 2-oxazolidinone; alkylene carbonate compounds such as ethylene carbonate; and the like. Of these compounds, from the viewpoint of maximizing an effect of a water absorbent property of the water absorbent resin in accordance with the present invention, one kind, or two or more kinds of the oxazolidinone compound(s), the alkylene carbonate compound(s), and the polyhydric alcohol compound(s) is/are preferably used. A C2-C10 polyhydric alcohol compound is more preferably used, and a C3-C8 polyhydric alcohol compound is still more preferably used. It is particularly preferable that such a polyhydric alcohol compound and the other surface-crosslinking agent (preferably an oxazolidinone compound or an alkylene carbonate compound) be used in combination.

A used amount of the surface-crosslinking agent (in a case where a plurality of surface-crosslinking agents are used, a total amount of the plurality of surface-crosslinking agents) is preferably 0.001 to 10 parts by weight, and more preferably 0.01 to 5 parts by weight, relative to 100 parts by weight of water absorbent resin powder, though depending on, for example, compounds to be used and a combination thereof. The surface-crosslinking agent which is used in an amount falling within the above range allows a further improvement in water absorbent property of the water absorbent resin of the present invention.

In an embodiment of the present invention, it is preferable to use water during the surface-crosslinking from the viewpoint of a physical property obtained after the surface-crosslinking. In this case, though depending on a moisture content of water absorbent resin powder to be used, water is used in an amount, preferably of 0.5 to 20 parts by weight, and more preferably of 0.5 to 10 parts by weight, relative to 100 parts by weight of the water absorbent resin powder. Besides water, a hydrophilic organic solvent is also usable. In this case, the hydrophilic organic solvent is used in an amount preferably of 0 to 5 parts by weight, and more preferably 0 to 3 parts by weight, relative to 100 parts by weight of the water absorbent resin powder.

A method in which the water or the hydrophilic organic solvent is added to or mixed with the water absorbent resin powder is not particularly limited. However, the water, the hydrophilic organic solvent, or a mixture of the water and the hydrophilic organic solvent is prepared in advance and then mixed with the water absorbent resin powder preferably by spray or drop, more preferably by spray. In a case where the mixing by spray is carried out, a liquid drop to be sprayed (the water, the hydrophilic organic solvent, or the mixture of the water and the hydrophilic organic solvent) has a size preferably of not more than 300 μm, and more preferably of not more than 200 μm. The liquid drop which has a size falling within the above range allows a further improvement in physical property of the water absorbent resin of the present invention which water absorbent resin has been surface-crosslinked. Further, water-insoluble microparticles or a surfactant may coexist with the water or the hydrophilic organic solvent and the water absorbent resin powder which are being mixed, provided that the coexistence does not impair an effect of a water absorbent property of the water absorbent resin in accordance with the present invention.

In the crosslinking step of the present invention, the water absorbent resin powder to/with which the surface-crosslinking agent has been added/mixed is preferably subjected to a heat treatment. In a case where the heat treatment is carried out, not only the surface-crosslinking agent reacts so as to adjust a water absorption capacity (CRC) and a water absorption capacity under load (AAP) of the water absorbent resin to fall within a preferable range (described later), but also an effect of preventing so-called gel blocking is obtained. The heat treatment is carried out at a temperature (a temperature of a mixture of the water absorbent resin powder and the surface-crosslinking agent) preferably of 100 to 250° C., and more preferably of 150 to 250° C. Further, the heat treatment is carried out preferably for 1 minute to 2 hours. Note that a combination of a time and a temperature during the heat treatment is preferably 0.1 to 1.5 hour at 180° C., and 0.1 to 1 hour at 200° C.

In a case where the surface-crosslinking is carried out until the water absorption capacity (CRC) decreases preferably to 1 to 20 [g/g], and more preferably to 2 to 15 [g/g] in a period in which the surface-crosslinking step has not been carried out and then has been carried out, water absorbent resin particles which have been surface-crosslinked have a higher water absorption capacity under load (AAP). As a result, the water absorbent resin which has been surface-crosslinked and a water absorbent agent composition to be obtained each has an AAP (specified in ERT442.2-02) preferably of not less than 15 [g/g], more preferably of 20 to 45 [g/g], still more preferably of 25 to 40 [g/g], and particularly preferably of 28 to 40 [g/g]. This allows the additional function (the deodorizing function in particular) provided to the water absorbent agent composition of the present invention to be more effectively carried out.

[3] Water Absorbent Agent Composition and Method for Producing the Water Absorbent Agent Composition (3-1) Water Absorbent Agent Composition The water absorbent agent composition in accordance with the present invention is a composition which contains not only a water absorbent resin serving as a main component but also a natural ingredient which allows the water absorbent agent composition to have an additional function, particularly a natural plant ingredient, and a temporal deterioration preventing agent which allows the water absorbent agent composition to continue to have the additional function even after the water absorbent agent composition is stored for a long term. Therefore, a case where no natural ingredient is used, or a case where only the temporal deterioration preventing agent is used may cause the additional function (the deodorizing function in particular) to be less effective, or cause a problem of safety and/or an odor. Therefore, such a case is not preferable.

Note that the water absorbent agent composition contains the water absorbent resin (a solid content of the water absorbent resin) in a ratio preferably of not less than 50 wt % and less than 100 wt %, more preferably of 60 to 99.9 wt %, still more preferably of 70 to 99 wt %, and particularly preferably of 80 to 98.9 wt %. The water absorbent resin contained in a ratio falling within the above range allows an improvement in water absorbent property of the water absorbent agent composition in accordance with the present invention. The water absorbent resin to be used a main component is not particularly limited. However, according to the present invention, from the viewpoint of a water absorbent property, the water absorbent resin is preferably water absorbent resin particles which have been surface-crosslinked.

(3-2) Natural Ingredient

A "natural ingredient" in accordance with the present invention is an ingredient which is capable of adding, to a water absorbent resin, functions such as deodorizing, anti-bacterial, and aromatizing functions, particularly preferably the deodorizing function, and refers to an ingredient which is produced by a living organism, more preferably a plant or animal-derived ingredient, and still more preferably a plant-derived ingredient (plant ingredient). Note that the natural ingredient in accordance with the present invention is most preferably a plant ingredient which is capable of adding the deodorizing function. Note also that the natural ingredient, which is an ingredient other than the water absorbent resin, contains no raw ingredient (e.g., graft component or main chain) for use in a method for producing the water absorbent resin.

The natural ingredient may be in a form of a natural ingredient purified as a single-component compound. However, since excessive purification is economically disadvantageous, the natural ingredient, which may be in a form of a mixture, is exemplified by a natural product per se such as plant powder, essence (essential oil) extracted from a natural product, and plant sediment or essence sediment obtained as a by-product during a production process of a food-processing industry or a foodstuff-processing industry. From the viewpoint of easiness of addition to the water absorbent resin and uniformity of mixing with the water absorbent resin, the natural ingredient may be in a form of a liquid or an aqueous solution at a normal temperature (20 to 25° C., particularly ° C.). An ingredient which is a solid at a normal temperature may be mixed in a form of powder, but is more preferably mixed in a form of an aqueous solution to the water absorbent resin.

In a case where the natural ingredient of the present invention is a natural product per se such as the plant powder or an ingredient which is a solid at a normal temperature and has been extracted from a natural product, or essence (essential oil)-supported powder, such a natural ingredient has a particle diameter normally of 0.001 to 1000 μm, and preferably of 1 to 600 μm. Further, such powder has a weight average particle diameter (D50) preferably of not more than 500 μm, and more preferably of not more than 300 μm. The weight average particle diameter (D50) which exceeds 500 μm causes an action of an effective ingredient contained in the natural ingredient to be insufficient when a body fluid such as human urine is brought into contact with the water absorbent agent composition. This may make it impossible to stably add the functions such as the deodorizing, antibacterial, and aromatizing functions. Note that the natural ingredient-supported powder is preferably smaller in weight average particle diameter (D50) than the water absorbent resin since it is possible to more stably provide the water absorbent resin with the functions such as the deodorizing function. Further, in a case where a powder ingredient such as the plant powder is mixed by a dry blend method (described later), a binder is also preferably added. The binder is preferably water, polyhydric alcohol, C3-C6 polyol, polyethylene glycol, or the like. That is, a water absorbent agent in accordance with the present invention preferably contains polyol. Polyol is suitably contained in an amount falling within a range (described later).

A raw plant of the plant ingredient which is capable of adding the deodorizing function (described earlier) is exemplified by Theaceae, Rubiaceae, Gramineae, Fagaceae, and the like, and is more preferably exemplified by Theaceae and Gramineae. Note that a plant belonging to Theaceae is exemplified by a camellia, a sasanqua, a tea plant, *Eurya japonica, Ternstroemia japonica*, and the like, and is more preferably exemplified by a tea plant. A plant belonging to Rubiaceae is exemplified by a madder, a coffee tree, *Morinda citrifolia*, and the like, and is more preferably exemplified by a coffee tree. A plant belonging to Gramineae is exemplified by rice, bamboo grass, a bamboo, corn, wheat, and the like, and is more preferably exemplified by bamboo grass and a bamboo. A plant belonging to Fagaceae is exemplified by *Fagus crenata, Quercus serrata, Quercus crispula*, an oak, and the like, and is more preferably exemplified by an oak. Further, the plant ingredient which is capable of adding the deodorizing function is also exemplified by green tea, black tea, oolong tea, Pu'er tea, and the like which is obtained by processing a leaf or a stem of the tea plant.

A plant-derived ingredient which is capable of adding the deodorizing function is exemplified by polyphenol, caffeine, and the like each contained in a plant, and is preferably exemplified by polyphenol, caffeine, and the like each contained in plants such as Theaceae, Rubiaceae, Gramineae, and Fagaceae, and is particularly preferably exemplified by polyphenol contained in a plant.

As the polyphenol contained in the plant, polyphenol containing flavonoid, phenylic acid, ellagic acid, lignan, curcumin, and coumalin is preferable, polyphenol containing flavonoid, ellagic acid, and lignan is more preferable, and polyphenol containing flavonoid is still more preferable. The flavonoid preferably contains catechin, anthocyanin, tannin, rutin, and isoflavone, and more preferably contains catechin and tannin. The catechin is preferably exemplified by tea catechin and a derivative thereof. The tannin is exemplified by hydrolyzable tannin and condensed tannin, and condensed tannin is more preferable.

In an embodiment of the present invention, at least one kind, preferably two or more kinds, and more preferably three or kinds of plant ingredient(s) selected from polyphenol containing flavonoid such as catechin, tannin, and isoflavone; caffeine; and the like may be contained as a natural ingredient in an amount of more than 0 and not more than 100 wt %. It is preferable that the plant ingredient be exemplified by at least one kind selected from tannin, tannic acid, a nutgall, a gallnut, and a gallic acid. A molecular weight of polyphenol is appropriately selected, and the molecular weight is preferably 500 to 20000, and is more preferably 1000 to 10000. The tannin is exemplified by hydrolyzable tannin and condensed tannin, and condensed tannin is more preferable.

It is only necessary that a used amount of the natural ingredient be appropriately determined in accordance with an intended additional function of the natural ingredient. The natural ingredient is used in an amount preferably of 0.00001 to 15 wt %, more preferably of 0.0001 to 10 wt %, still more preferably of 0.001 to 7 wt %, and particularly preferably of 0.01 to 6 wt %, relative to the solid content of the water absorbent resin. In a case where the used amount of the natural ingredient is less than 0.00001 wt %, it may be impossible to provide a sufficient additional function. Meanwhile, in a case where the used amount of the natural ingredient is more than 15 wt %, it may be impossible to obtain an effect corresponding to the used amount. Note that the used amount of the natural ingredient is specified by a solid content excluding a solvent in a case where the natural ingredient is added in a form of a solution.

The used amount of the natural ingredient can also be determined by use of a total contained amount of caffeine and/or catechins, or a contained amount of tannin. In this case, it is only necessary that the used amount of the natural ingredient be determined so that the total contained amount of caffeine and/or catechins is preferably 0.5 ppm to 1 wt %, more preferably 10 ppm to 0.5 wt %, still more preferably 20 ppm to 0.1 wt %, and particularly preferably 50 ppm to 0.1 wt %, relative to the solid content of the water absorbent resin. Note that the total contained amount of caffeine and/or catechins is found by extracting the water absorbent agent composition by use of, for example, water, a physiological saline solution, or a water-alcohol mixed solvent, concentrating a resulting extract according to need, and then quantitatively analyzing the extract by liquid chromatography or the like. Meanwhile, the contained amount of tannin is found by extracting a water absorbent agent composition by use of, for example, water, a physiological saline solution, or a water-alcohol mixed solvent, concentrating/drying and solidifying a resulting extract according to need, and then quantitatively analyzing the extract by, for example, absorption photometry by use of a Folin reagent or the like.

It is preferable that any one of the used amount of the natural ingredient, the total contained amount of caffeine and/or catechins, and the contained amount of tannin be satisfied. It is more preferable that both the used amount of the natural ingredient and the total contained amount of caffeine and/or catechins, or the contained amount of tannin be satisfied.

(3-3) Temporal Deterioration Preventing Agent

A "temporal deterioration preventing agent" in accordance with the present invention refers to a compound which is added so as to maintain an additional function (prevent a deterioration) even after a water absorbent agent composition having the additional function (a deodorizing function in particular) is stored for a long term (not less than 30 days) until the water absorbent agent composition is actually used. Specifically, synthetic or natural ingredients such as an antioxidant, a preservative, a germicide, an antibacterial agent, an antiseptic agent, and an antifungal agent, particularly the synthetic ingredients fall under the temporal deterioration preventing agent. In particular, ingredients other than the natural ingredients are preferable, and artificial synthetic ingredients are more preferable.

It is only necessary that a used amount of the temporal deterioration preventing agent be appropriately determined in accordance with an intended use of the temporal deterioration preventing agent. The temporal deterioration preventing agent is used in an amount preferably of 0.05 to 120 ppm, and more preferably of 0.1 to 100 ppm, relative to the solid content of the water absorbent resin. In a case where the used amount of the temporal deterioration preventing agent is less than 0.1 ppm, it may be impossible to provide the water absorbent resin of the present invention with a sufficient deterioration preventing effect. Meanwhile, in a case where the used amount of the temporal deterioration preventing agent is more than 100 ppm, when the water absorbent agent composition is used as an absorbent article such as a paper diaper, more stress is placed on dermis (skin), so that problems of skin roughness, diaper rash, and the like may occur. Note that the used amount of the temporal deterioration preventing agent is specified by a solid content excluding a solvent such as a hydrophilic solvent in a case where the temporal deterioration preventing agent is added in a form of a solution.

Further, an optimum used amount of the temporal deterioration preventing agent varies depending on a combination of the natural ingredient to be used and the temporal deterioration preventing agent to be used. Specifically, it is desirable to determine the used amount of the temporal deterioration preventing agent so that a rate of reduction in additional function which rate is specified by a percentage of an amount of reduction in natural ingredient when the natural ingredient is stored at a normal temperature (25° C.) for 30 days in a form of an aqueous solution (particularly a 1 wt % aqueous solution) is preferably not more than 50%, more preferably not more than 10%, and still more preferably not more than 1%.

A weight ratio of the temporal deterioration preventing agent to the natural ingredient (described earlier) (temporal deterioration preventing agent/natural ingredient) is preferably 1/10000 to 1/10, more preferably 1/8000 to 1/50, and still more preferably 1/6000 to 1/100. The weight ratio which is beyond the above range may make it impossible to obtain a sufficient deterioration preventing effect, may cause the temporal deterioration preventing agent which is in an excessive amount to be economically disadvantageous, and may cause a problem of, for example, skin roughness. Meanwhile, in a case where the temporal deterioration preventing agent is excessively used relative to the natural ingredient, some compounds (particularly a water-soluble oxidant, a water-soluble reducing agent, or the like) may cause a deterioration in water absorbent resin depending on a kind of the temporal deterioration preventing agent. Accordingly, it is preferable that the temporal deterioration preventing agent be used in a smaller amount than the natural ingredient.

It is only necessary that the temporal deterioration preventing agent be powder or a liquid at a normal temperature (20 to 25° C., particularly 25° C.). Furthermore, the temporal deterioration preventing agent can also be added, in a form of a solution containing a hydrophilic solvent, e.g., an aqueous solution, to the water absorbent resin. Moreover, in order that the additional function of the natural ingredient is maintained, it is more preferable that the temporal deterioration preventing agent be added to the water absorbent resin while being mixed with the natural ingredient.

The temporal deterioration preventing agent is not particularly limited provided that the temporal deterioration preventing agent maintains or improves the additional function (the deodorizing function in particular) of the water absorbent agent composition. However, at least one kind selected from, for example, an antioxidant, a preservative, a germicide, an antibacterial agent, an antiseptic agent, and an antifungal agent (which are described earlier) falls under the temporal deterioration preventing agent.

Specific examples of the antioxidant include: phenolic antioxidants such as 2,6-di-t-butyl-p-cresol (BHT) and 2,2'-methylenebis(4-methyl-6-t-butylphenol); sulfuric antioxidants such as dilauryl-3,3'-thiodipropionate (DLTDP) and distearyl-3,3'-thiodipropionate (DSTDP); phosphorous antioxidants such as triphenyl phosphite (TPP) and triisodecyl phosphite (TDP); amine antioxidants such as octylated diphenylamine, N-n-butyl-p-aminophenol, and N,N-diisopropyl-p-phenylenediamine; ascorbic acids such as L-ascorbic acid, sodium L-ascorbate, D-ascorbic acid, and sodium D-ascorbate; erythorbic acids such as erythorbic acid and sodium erythorbate; gallic acids such as gallic acid, methyl gallate, ethyl gallate, n-propyl gallate, isoamyl gallate, octyl gallate, and lauryl gallate; protocatechuic acids such as protocatechuic acid and protocatechuic acid ethyl; benzimidazoles such as 2-mercaptobenzimidazole; alkyl hydroxyanisoles such as butylhydroxyanisole; and the like.

The preservative is specifically exemplified by sorbic acid and the like.

Specific examples of the germicide or the antibacterial agent include tetrachloroisophthalonitrile (TPN), Captan, a vinclozolin agent, a procymidone agent, a bench azole agent, a quaternary ammonium salt, a phenolic compound, a quaternary pyridinium salt, peracid, formaldehyde, antibiotics (for example, penicillin, streptomycin, chloramphenyl alcohol, etc.), N-chlorosuccinimide, lime, sulfur, organic sulfur agents (for example, zineb, maneb, a thiodiazine agent, a thiuram agent, etc.), monothiocarbamate, dithiocarbamate, thiodiazine, sulfonamide, phthalimide, petroleum ether, naphthoquinone, benzoquinone, disulfide, a mercuric compound, tetrahydrophthalimide, arsenate, a cupric salt, an organic copper agent (8-hydroxyquinoline copper etc.), guanidine salt, triazine, glyoxal-lysine salt, quinolinium salt, phenylcrotonate, and the like.

Specific examples of the antiseptic agent or the antifungal agent include halogen supply agents, particularly chlorine supply agents such as chloro-cyanuric acids or salts thereof, particularly dichloroisocyanuric acid mono-sodium or potassium; hydroxyquinones, a sulfite, silver salt, copper salt, and the like.

Of the temporal deterioration preventing agents described earlier, the temporal deterioration preventing agent is preferably at least one kind of a compound selected from: water-soluble reducing agents selected from, for example, erythorbic acid, L-ascorbic acid, and sulfites; water-soluble oxidants selected from, for example, hypochlorous acids and hypochlorites as a preservative, a germicide, an antiseptic agent, and an antifungal agent; phenylphenols (excluding methoxyphenols) such as o-phenylphenol as a germicide and an antifungal agent; benzoic acid or esters thereof (preferably C1-C20 alkyl ester, and more preferably C1-C10 alkyl ester) as a germicide; and hydroxybenzoic acid or esters thereof (preferably C1-C20 alkyl ester, and more preferably C1-C10 alkyl ester) as a germicide. The temporal deterioration preventing agent is more preferably a benzoic acid or a benzoic acid ester, or a hydroxybenzoic acid or a hydroxybenzoic acid ester.

Specific examples of the benzoic acid ester include methylparaben (4-hydroxy-benzoic acid methyl), ethylparaben (4-hydroxy-benzoic acid ethyl), propylparaben (4-hydroxy-benzoic acid propyl), isopropylparaben (4-hydroxy-benzoic acid isopropyl), butylparaben (4-hydroxy-benzoic acid butyl), isobutylparaben (4-hydroxy-benzoic acid isobutyl), benzilparaben (4-hydroxy-benzoic acid benzil), and the like, and paraben selected from these benzoic acid esters is preferably used. The hydroxybenzoic acid is specifically exemplified by gallic acid, and the hydroxybenzoic acid ester is specifically exemplified by propyl gallate.

Of the temporal deterioration preventing agents selected from, for example, the antioxidants, the preservatives, the germicides, the antibacterial agents, the antiseptic agents, and the antifungal agents, an antioxidant and a preservative are more preferable. At least one kind of a compound selected from: ascorbic acids such as L-ascorbic acid, sodium L-ascorbate, D-ascorbic acid, and sodium D-ascorbate; erythorbic acids such as erythorbic acid and sodium erythorbate; sorbic acids such as potassium sorbate and sodium sorbate; gallic acid, methyl gallate, ethyl gallate, n-propyl gallate, isoamyl gallate, octyl gallate, and lauryl gallate; and benzoic acids such as sodium benzoate, methylparaben (4-hydroxy-benzoic acid methyl), ethylparaben (4-hydroxy-benzoic acid ethyl), propylparaben (4-hydroxy-benzoic acid propyl), isopropylparaben (4-hydroxy-benzoic acid isopropyl), butylparaben (4-hydroxy-benzoic acid butyl), and benzilparaben (4-hydroxy-benzoic acid benzil) is still more preferable. At least one kind of a compound selected from erythorbic acids, sorbic acids, and benzoic acids is still more preferable. At least one kind of a compound selected from benzoic acids is particularly preferable. In particular, a benzoic acid (salt) or an ester thereof, or a hydroxybenzoic acid (salt) or an ester thereof is more preferable, and a hydroxybenzoic acid ester is the most preferable.

(3-4) Method for Producing Water Absorbent Agent Composition

A water absorbent agent composition in accordance with the present invention can be obtained by adding a natural ingredient and a deterioration preventing agent to water absorbent resin particles described in the above [2], and mixing the natural ingredient and the deterioration preventing agent with the water absorbent resin particles. However, a method for producing the water absorbent agent composition is not particularly limited. For example, the method for producing the water absorbent agent composition is exemplified by a method in which a mixture of a natural ingredient and a temporal deterioration preventing agent is added to a water absorbent resin; a method in which a natural ingredient and a temporal deterioration preventing agent are separately added to a water absorbent resin; and the like.

Further, in a case where the natural ingredient and/or the temporal deterioration preventing agent are/is a liquid material(s), specifically in a case where the natural ingredient and/or the temporal deterioration preventing agent are/is a liquid(s) at a normal temperature (20 to 25° C., particularly 25° C.), or in a case where the natural ingredient and/or the temporal deterioration preventing agent are/is a solution(s) obtained by dissolving the natural ingredient and/or the temporal deterioration preventing agent in, for example, water, an aqueous solution, an organic solvent, or the like the method for producing the water absorbent agent composition is exemplified by a method in which the natural ingredient and/or the temporal deterioration preventing agent are/is spray or drop-mixed with the water absorbent resin so that the natural ingredient and/or the temporal deterioration preventing agent are/is added to the water absorbent resin in a desired amount. Meanwhile, in a case where the natural ingredient and/or the temporal deterioration preventing agent are/is powder, the method for producing the water absorbent agent composition is exemplified by a method in which the natural ingredient and/or the temporal deterioration preventing agent are/is directly mixed with the water absorbent resin so that the natural ingredient and/or the temporal deterioration preventing agent are/is added to the water absorbent resin in a desired amount (e.g., a dry blend method in the case of mixing of minute particles); a method in which, in order that the natural ingredient and/or the temporal deterioration preventing agent are/is added to the water absorbent resin in a desired amount, water, an aqueous solution, an organic solvent, or the like is spray or drop-mixed with the natural ingredient and/or the temporal deterioration preventing agent which have/has been directly mixed with the water absorbent resin; and the like. It is considered that the natural ingredient and the temporal deterioration preventing agent are preferably close to each other in the water absorbent resin so that a greater effect of the present invention is obtained. Therefore, it is preferable that the natural ingredient and the temporal deterioration preventing agent be added simultaneously, and it is more preferable that the natural ingredient and the temporal deterioration preventing agent be added in a form of a mixture.

A timing at which the natural ingredient and/or the temporal deterioration preventing agent are/is added is not particularly limited. It is possible to add the natural ingredient and/or the temporal deterioration preventing agent at each production step carried out during production of the water absorbent agent composition, or after the production step. Specifically, it is only necessary to add the natural ingredient and/or the temporal deterioration preventing agent preferably during a step carried out on and after the polymerization step, more preferably during a step carried out on and after the drying step, and still more preferably during a step carried out on and after the heat treatment in the surface-crosslinking step, during the production of the water absorbent resin. Accordingly, specifically, the natural ingredient and/or the temporal deterioration preventing agent may be added to a hydrous gelatinous crosslinked polymer obtained at polymerization or after polymerization. However, in view of a deterioration and/or colorability of the natural ingredient due to heating, it is particularly preferable to add the natural ingredient and/or the temporal deterioration preventing agent after a step of the heat treatment in the surface-crosslinking is ended (e.g., during a cooling step). Note that in view of a deterioration and/or colorability of the natural ingredient, the water absorbent resin has a temperature (powder temperature) preferably of 0 to 150° C., more preferably of 40 to 100° C., and still more preferably of 50 to 90° C. during the addition of the natural ingredient and/or the temporal deterioration preventing agent. The water absorbent resin which has a temperature (powder temperature) falling within the above range makes it possible to prevent a decrease in additional function of the natural ingredient contained in the water absorbent agent composition in accordance with the present invention, and to prevent coloring of the water absorbent agent composition.

An optimum amount of water, water vapor, an aqueous solution containing water and a hydrophilic organic solvent, or the like which is added according to need during the addition of the natural ingredient and/or the temporal deterioration preventing agent varies in accordance with, for example, a kind and a particle size of the water absorbent resin. However, for example, water is added in an amount preferably of not more than 10 parts by weight, and more preferably of 1 to 5 parts by weight, relative to 100 parts by weight of a solid content of the water absorbent resin. Meanwhile, for example, an aqueous solution containing water and a hydrophilic organic solvent is added in an amount preferably of not more than 10 parts by weight, and more preferably of 0.1 to 5 parts by weight, relative to 100 parts by weight of a solid content of the water absorbent resin. Further, the hydrophilic organic solvent is contained in the aqueous solution in an amount of 0 to 100 wt %, preferably in an amount of 1 to 50 wt %, and more preferably in an amount of 5 to 40 wt %.

A liquid temperature of an aqueous solution in a case where the natural ingredient and/or the temporal deterioration preventing agent are/is added in a form of a solution is appropriately determined. The aqueous solution may be heated in view of its solubility and viscosity, and has a liquid temperature preferably of 0 to 100° C., and more preferably of 20 to 50° C. As described earlier, in a case where the natural ingredient and/or the temporal deterioration preventing agent are/is added in a form of a mixture, the natural ingredient and/or the temporal deterioration preventing agent are/is preferably added in a form of a solution (an aqueous solution or a water dispersion) to the water absorbent resin, and the natural ingredient contained in the aqueous solution or the water dispersion has a concentration of 0.1 to 80 wt %, and more preferably of 1 to 70 wt %. Use of the hydrophilic organic solvent allows more uniform mixing. This makes it possible to reduce occurrence of a lump during mixing with the water absorbent resin and a load on (damage to) the water absorbent agent composition. Further, use of water accelerates spreading and fixation to the water absorbent resin. In a case where the natural ingredient is added to the water absorbent resin by being diluted with, for example, a solvent, it is preferable that the natural ingredient be mixed with the water absorbent resin in minimal time (particularly within 24 hours) after being diluted at a concentration for being added.

Examples of the hydrophilic organic solvent include alcohols such as methyl alcohol, ethyl alcohol, propyl alcohol, isopropyl alcohol, butyl alcohol, isobutyl alcohol, and t-butyl alcohol; ketones such as acetone and methylethylketone; ethers such as dioxane, alkoxy(poly)ethylene glycol, and tetrahydrofuran; amides such as ε-caprolactam and N,N-dimethylformamide; sulfoxides such as dimethyl sulfoxide; polyhydric alcohols such as ethylene glycol, diethylene glycol, propylene glycol, triethylene glycol, tetraethylene glycol, 1,3-propanediol, dipropylene glycol, 2,2,4-trimethyl-1,3-pentanediol, glycerine, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, pentaerythritol, and sorbitol; and the like. It is possible to use one kind, or two or more kinds of these hydrophilic organic solvent(s).

The hydrophilic organic solvent is preferably an alcohol or polyhydric alcohol, more preferably a C2-C6 alcohol or polyhydric alcohol, still more preferably a C3-C5 alcohol or polyhydric alcohol, and particularly preferably a C3-C5 polyhydric alcohol. The hydrophilic organic solvent is specifically exemplified preferably by ethyl alcohol, isopropyl alcohol, propylene glycol, and glycerine, and particularly preferably by ethyl alcohol and propylene glycol. That is, the water absorbent agent composition in accordance with the present invention preferably contains polyol. The water absorbent agent composition which contains polyol is preferable since polyol allows maintenance of a water absorption capacity under load and a reduction in dust. Though the mixed hydrophilic organic solvent, particularly polyol may be dried (removed) after mixing, react, or partially or entirely remain, a given amount of polyol is preferably contained in the water absorbent agent composition.

The hydrophilic organic solvent, particularly polyol is contained or used in an amount preferably of 0 to 10 parts by weight, more preferably of 0.001 to 5 parts by weight, and still more preferably of 0.01 to 1 part by weight, relative to 100 parts by weight of the water absorbent resin. An amount of the hydrophilic organic solvent contained in the water absorbent agent composition can be appropriately controlled in accordance with a mixed amount (a heating temperature and time in a case where heating is carried out after mixing).

Note that a polyhydric alcohol may be arranged such that a polyhydric alcohol derived from a reaction of alkylene carbonate, e.g., ethylene glycol derived from ethylene carbonate, or propylene glycol derived from propylene carbonate remains on a surface of the water absorbent resin.

Further, in addition to the natural ingredient and/or the temporal deterioration preventing agent, and the solvent (water/hydrophilic organic solvent), other ingredients such as a chelating agent and a surfactant may be simultaneously or separately mixed.

A mixing apparatus which is used to add the natural ingredient and/or the temporal deterioration preventing agent to the water absorbent resin is exemplified by but not particularly limited to a cylindrical mixer, a screw mixer, a screw extruder, a turbulizer, a Nauta mixer, a V-shaped mixer, a ribbon mixer, a dual-arm kneader, a flow mixer, an air mixer, a rotating disc mixer, a roll mixer, a tumbling mixer, and the like. Note that a speed at which the mixing apparatus rotates is not particularly required. The mixing apparatus may rotate at either a high speed or a low speed.

In order that the additional function (the deodorizing function in particular) are more effectively carried out, it is desired in a process for producing the water absorbent resin and the water absorbent agent composition that at least one, more preferably two or more (particularly a combination of (b) and (a) or (c)), still more preferably three or more (particularly a combination of (a), (b), and (c)), particularly preferably all four of steps specified by the following (a) through (d) be satisfied.

(a) a polymerization step or a chelating agent addition step of causing the water absorbent resin to have a degradable soluble component of not more than 40 wt %;

(b) a classification step of causing the water absorbent resin to contain particles having a particle diameter (specified by a standard sieve) of not less than 150 μm and less than 850 μm in an amount of not less than 90 wt % of the total water absorbent resin, and causing the water absorbent resin to contain particles having a particle diameter (specified by a standard sieve) of not less than 300 μm in an amount of not less than 60 wt %;

(c) a surface-crosslinking step of causing the water absorbent resin to have a water absorption capacity under load (AAP) of not less than 15 [g/g]; and (d) a step of mixing water-insoluble microparticles.

A chelating agent used in the chelating agent addition step enhances an effect yielded by the natural ingredient and/or the temporal deterioration preventing agent. Therefore, the water absorbent agent composition in accordance with the present invention more preferably contains a chelating agent. The chelating agent, which may be either a polymerized compound or a non-polymerized compound, is preferably a non-polymerized compound, from the viewpoint of effect. Specifically, the chelating agent is preferably a polyvalent compound selected from amino-polyvalent carboxylic acid, organic polyvalent phosphoric acid, inorganic polyvalent phosphoric acid, and amino-polyvalent phosphoric acid. The chelating agent has a molecular weight preferably of 100 to 5000, and more preferably of 200 to 1000. Use of a suitable chelating agent makes it possible to obtain the water absorbent agent composition which further has a coloring preventing function and a deterioration preventing function.

A polyvalent compound which is taken as an example of the chelating agent is a compound which contains, in one molecule, a plurality of functional groups, preferably 2 to 30 functional groups, more preferably 3 to 20 functional groups, and still more preferably 4 to 10 functional groups. Further, such a chelating agent is preferably a water-soluble chelating agent. Specifically, the chelating agent is preferably a water-soluble chelating agent to be dissolved in 100 g of water (25° C.) in an amount of not less than 1 g, and still more preferably a water-soluble chelating agent to be dissolved in 100 g of water (25° C.) in an amount of not less than 10 g.

Examples of the amino-polyvalent carboxylic acid include iminodiacetic acid, hydroxyethyl iminodiacetic acid, nitrilotriacetic acid, nitrilotripropionic acid, ethylenediamine tetraacetic acid, diethylenetriamine pentaacetic acid, triethylene tetramine hexaacetic acid, trans-1,2-diaminocyclohexane tetraacetic acid, N,N-bis(2-hydroxyethyl)glycine, diaminopropanol tetraacetic acid, ethylenediamine dipropionic acid, hydroxyethylenediamine triacetic acid, glycol ether diaminetetraacetic acid, diaminopropane tetraacetic acid, N,N'-bis(2-hydroxybenzil)ethylenediamine-N,N'-diacetic acid, 1,6-hexamethylendiamine-N,N,N',N'-tetraacetic acid, salts of these amino-polyvalent carboxylic acids, and the like.

Examples of the organic polyvalent phosphoric acid include nitriloacetic acid-di(methylenephosphinic acid), nitrilodiacetic acid-(methylenephosphinic acid), nitriloacetic acid-β-propionic acid-methylenephosphonic acid, nitrilotris(methylenephosphonic acid), 1-hydroxyethylidenediphosphonic acid, and the like. Examples of the inorganic polyvalent phosphoric acid include pyrophosphoric acid, tripolyphosphoric acid, salts of these inorganic polyvalent phosphoric acids, and the like.

Examples of the amino-polyvalent phosphoric acid include ethylenediamine-N,N'-di(methylenephosphinic acid), ethylenediaminetetra(methylenephosphinic acid), cyclohexanediaminetetra(methylenephosphonic acid), ethylenediamine-N,N'-diacetic acid-N,N'-di(methylenephosphonic acid), ethylenediamine-N,N'-di(methylenephosphonic acid), ethylenediaminetetra(methylenephosphonic acid), polymethylenediaminetetra(methylenephosphonic acid), diethylenetriaminepenta(methylenephosphonic acid), salts of these amino-polyvalent phosphoric acids, and the like.

It is only necessary that the chelating agent be present on an inside or a surface of the water absorbent resin. The chelating agent is added to the inside or the surface of the water absorbent agent composition by being appropriately mixed by, for example, being mixed with monomers which are being polymerized, being mixed with a hydrogel which has been obtained by the polymerization and has not been dried, or being mixed with water absorbent resin powder which is obtained after the drying.

The polymerization step or the addition of the chelating agent may cause the water absorbent resin to have a degradable soluble component of not more than 40 wt %. The present invention preferably includes the chelating agent addition step, and it is more preferable in the present invention to mix the chelating agent during or after the polymerization. The chelating agent is added preferably in an amount of 0 to 5 wt %, more preferably in an amount of 10 ppm to 1 wt %, still more preferably in an amount of 50 to 5000 ppm, and particularly preferably in an amount of 100 to 2000 ppm, relative to the water absorbent resin. The degradable soluble component may be adjusted to not more than 40 wt % in the polymerization step by a method other than the addition of the chelating agent, e.g., by highly crosslinking the water absorbent resin during the polymerization (e.g., using a crosslinking agent in an amount of not less than 0.1 mol %), or by using a water-soluble chain transfer agent (e.g., using hypophosphite in an amount of 0.01 to 1 mol % relative to monomers). However, a method of the addition of the chelating agent is more preferable from the viewpoint of a physical property.

Further, the water absorbent agent composition in accordance with the present invention such as a particulate water absorbent agent preferably contains Fe in a smaller amount from the viewpoint of not only deodorization but also prevention of a deterioration and coloring thereof. As to Fe contained in the water absorbent agent composition, it is preferable that Fe be derived mainly from a base used for neutralization and contained in an amount (as a weight of Fe contained in the water absorbent agent composition) preferably of not more than 2 ppm, more preferably of not more than 1.5 ppm, still more preferably of 1 ppm, and particularly preferably of not more than 0.5 ppm. A lower limit of an amount of Fe is preferably 0.001 ppm, and more preferably 0.01 ppm.

The amount of iron (Fe) is controlled mainly by controlling a base (particularly caustic soda) which is used for neutralization. Besides, the control of the amount of iron (Fe) is also carried out by, for example, controlling trace iron of raw materials (acrylic acid, a crosslinking agent, water, etc.), or by controlling material properties of a resin coating, a glass coating, stainless steel, and the like of various water absorbent resin producing apparatuses such as a polymerization apparatus and a monomer pipe, and a pipe. Note that amounts of iron contained in the base and the water absorbent agent composition can be determined quantitatively by an ICP emission spectrochemical analysis method described in JIS K1200-6, for example, and International Publication No. 2008/090961 can be referred to as a reference on a quantitative determination method.

In a case where the step of mixing water-insoluble microparticles is carried out, handleability of the water absorbent resin and the water absorbent agent composition as powder, particularly flowability of powder under moisture absorption is enhanced. The water-insoluble microparticles used in this step is exemplified by but not particularly limited to metallic oxides such as silicon dioxide and titanic oxide; silicic acids and silicates such as natural zeolite and synthetic zeolite; and inorganic powder such as kaolin, talc, clay, and bentonite. Of these water-insoluble microparticles, silicon dioxide and silicic acids and silicates are preferable. The water-insoluble microparticles have an average particle diameter (measured by a Coulter counter method) preferably of not more than 200 μm, more preferably of 0.001 to 100 μm, and still more preferably of 0.01 to 10 μm.

Though depending on a combination of the water absorbent agent composition or the water absorbent resin and the water-insoluble microparticles, the water-insoluble microparticles are added in an amount preferably of 0.001 to 10 parts by weight, more preferably of 0.01 to 5 parts by weight, still more preferably of 0.01 to 3 parts by weight, and particularly preferably of 0.01 to 1 part by weight, relative to 100 parts by weight of the water absorbent agent composition or the water absorbent resin. In a case where the water-insoluble microparticles are added in an amount falling within the above range, a water absorption capacity under load of the water absorbent agent composition or the water absorbent resin can be maintained at a comparatively high level while a moisture absorption blocking rate and permeability of the water absorbent agent composition or the water absorbent resin of the present invention are maintained at a high level, or a reduction in water absorption capacity under load (AAP) due to the water-insoluble microparticles can be prevented. A method for mixing the water-insoluble microparticles is exemplified by but not particularly limited to a dry blend method in which microparticles are mixed, a wet blending method in which the water-insoluble microparticles are dispersed in a solution containing the natural ingredient and a surface-crosslinking agent, or in water, and the like. Of these methods, the dry blend method is more preferable from the viewpoint of a mixing efficiency.

(3-5) Physical Properties of Water Absorbent Agent Composition (a) Water Absorption Capacity without Load (CRC) (ERT441.2-02)

The water absorbent agent composition in accordance with the present invention has, as a later-mentioned water absorbent agent, a water absorption capacity without load (CRC) preferably of 10-100 [g/g], more preferably of 20-80 [g/g], still more preferably of 25-45 [g/g], and particularly preferably of 30-40 [g/g]. A water absorption capacity without load (CRC) of the water absorbent agent composition of the present invention being within the above range is preferable since this range allows sanitary goods such as paper diapers including the water absorbent agent composition to be excellent in performance of absorbing and retaining a body fluid such as urine and reduce an amount of the water absorbent agent composition used therein.

(b) Water Soluble Component (Ext) (ERT470.2-02)

The water absorbent agent composition in accordance with the present invention has, as the later-mentioned water absorbent agent, a water soluble component (Ext) preferably of not more than 50 wt %, more preferably of not more than 25 wt %, still more preferably of not more than 20 wt %, particularly preferably of not more than 15 wt %, and most preferably of not more than 10 wt %. The water soluble component (Ext) of the water absorbent agent composition of the present invention being within the above range is preferable since this range allows a reduction in stickiness when the water absorbent agent composition is used in paper diapers etc.

(c) Moisture content (ERT430.0-02)

The water absorbent agent composition in accordance with the present invention has, as the later-mentioned water absorbent agent, a moisture content preferably of 0.2-30 wt %, more preferably of 0.3-20 wt %, still more preferably of 1.0-15 wt %, particularly preferably of 1.5-10 wt %, and most preferably of 2.0-10 wt %. The moisture content of the water absorbent agent composition of the present invention being within the above range is preferable since this range allows the water absorbent agent composition to carry out the additional function more effectively, and to show flowability at normal temperatures, so that the water absorbent agent composition becomes powder with excellent handleability and has improved productivity.

(d) Deodorizing Test a and Stabilization Index

As for the water absorbent agent composition in accordance with the present invention, it is preferable that the results of evaluation in deodorizing tests A carried out at the start and the end, respectively, of a test on stability in maintaining a deodorizing effect of the water absorbent agent composition are each not more than 3.3, and a stabilization index is in a range of 90 to 100%. The result of evaluation in the deodorizing test A being not less than 3.4 is not preferable since such a value indicates that the deodorizing effect is insufficient. Furthermore, the stabilization index being within the above range is preferable since this range allows a reduction in variation in deodorizing function of a later-mentioned water absorbent core and/or absorbent article (such as paper diapers).

(e) Degradable Soluble Component

The water absorbent agent composition in accordance with the present invention has a degradable soluble component preferably of not more than 40 wt %, more preferably of not more than 30 wt %, and still more preferably of not more than 25 wt %. The lower limit of the degradable soluble component is not less than 5 wt % in consideration of balance with other physical properties (water absorption capacity in particular). The degradable soluble component being not less than 40 wt % is not preferable since such a value may raise problems such as a deterioration in gel, skin roughness, rash, a deterioration in ability to remove offensive odor due to a body fluid such as urine, when the water absorbent agent composition is used for the later-mentioned water absorbent core and/or absorbent article (such as paper diapers).

The "degradable soluble component" indicates a water soluble component in consideration of a deterioration in gel due to urine, and is measured with a physiological saline solution to which L-ascorbic acid which promotes deterioration in gel is added (specified in the item (7-3) below).

(f) Moisture Absorption Blocking Ratio (BR)

The water absorbent agent composition in accordance with the present invention has a moisture absorption blocking ratio (BR) of not more than 30 wt %, more preferably of not more than 10 wt %, still more preferably of not more than 5 wt %, and particularly preferably of not more than 2 wt %. The moisture absorption blocking ratio (BR) being more than 30 wt % is not preferable since such a value may raise problems such as a problem such that worsened flowability of powder at a high humidity worsens handleability of the water absorbent agent composition, resulting in agglomeration and clogging of a water absorbent core in a production plant when the water absorbent core is prepared, or resulting in agglomeration and clogging of the water absorbent agent composition in a carrier pipe; and a problem such that the water absorbent agent composition cannot be evenly mixed with hydrophilic fibers.

(g) Others

Furthermore, the water absorbent agent composition in accordance with the present invention satisfies at least one of the following physical properties (1) through (4), more preferably two or more (particularly a combination of (2) and (1) or (3)), still more preferably three or more (particularly a combination of (1), (2), and (3)), particularly preferably all four of the physical properties.

(1) having a degradable soluble component of not more than 40 wt %, and more preferably of an amount falling within the range described in the above (e);

(2) containing particles having a particle diameter (specified by a standard sieve) of not less than 150 μm and less than 850 μm in an amount of not less than 90 wt % of the total water absorbent agent composition, and containing particles having a particle diameter (specified by a standard sieve) of not less than 300 μm in an amount of not less than 60 wt % of the total water absorbent agent composition, and more preferably of an amount falling within the range described in the above (2-5);

(3) having a water absorption capacity under load (AAP) (specified in ERT442.2-02) of not less than 15 [g/g], and more preferably of an amount falling within the range described in the above (2-6); and (4) having a moisture absorption blocking rate of not more than 30 wt %, and more preferably of an amount falling within the range described in the above (f).

[4] Water Absorbent Agent Package and Method for Storing or Stocking the Water Absorbent Agent Package The present invention also provides a package of the water absorbent agent composition and a method for storing or stocking the water absorbent agent package. The "water absorbent agent package" indicates various kinds of sealed containers such as a container bag, a paper bag, and a silo filled with the water absorbent agent composition. The water absorbent agent package can be transported, stored, or stocked. A unit of a filling amount of the water absorbent agent package is not particularly limited, but is preferably 1 kg to 100 t, more preferably 10 kg to 10 t, and still more preferably 20 kg to 2 t.

By packaging the water absorbent agent composition containing the natural ingredient and the temporal deterioration preventing agent in the form of the water absorbent agent package, it is possible to stably store or stock the water absorbent agent composition in a packed state for a long time, preferably for not less than 30 days, more preferably for not less than 60 days, and still more preferably for not more than 100 days (upper limit is 1000 days or so), and to maintain an additional function of the water absorbent agent composition, until the water absorbent agent composition is actually used.

[5] Water Absorbent Core

A "water absorbent core" of the present invention indicates a shaped matter whose main components are the water absorbent agent composition described in the item [3] and a fiber base material (also referred to as a fiber material). That is, the water absorbent core is a shaped matter made of materials having a water-absorbing ability, and is preferably a matter whose water absorbing materials are the water absorbent agent composition and the fiber base material and whose shape is retained by a binder, unwoven cloth etc. if necessary.

To be more specific, the water absorbent core indicates a water absorbent core containing: a particulate water absorbent agent composition whose main component is a water absorbent resin which has a crosslinked structure and is obtained by polymerizing acid radical-containing unsaturated monomers; and hydrophilic fiber which is a fiber basic material. The water absorbent agent composition contains the aforementioned natural ingredient and the temporal deterioration preventing agent. However, the present invention is not limited to this, and the absorbent article may be, for example, one obtained by adding a natural ingredient and a temporal deterioration preventing agent to a fiber base material such as hydrophilic fiber so that the fiber base material contains the natural ingredient and the temporal deterioration preventing agent.

The water absorbent core can be produced by forming the water absorbent agent composition and the hydrophilic fiber into a sheet shape, cylinder shape etc. Alternatively, the water absorbent core can be produced by using the water absorbent resin, the natural ingredient, the temporal deterioration preventing agent, and the hydrophilic fiber. Alternatively, the water absorbent core can be easily produced by blending the hydrophilic fiber, the water absorbent agent composition, and if necessary other fiber base material, an adhesive or etc., or causing the water absorbent agent composition to be sandwiched between fiber base materials such as hydrophilic fibers, or other method.

Furthermore, the water absorbent core of the present invention may be one obtained by causing the water absorbent agent composition to be sandwiched between fibers other than the hydrophilic fibers, such as tissue paper, or one obtained by solidifying the water absorbent agent composition with an adhesive etc.

A core concentration, which is defined as a contained amount of the water absorbent agent composition relative to a total weight of the water absorbent agent composition and the hydrophilic fiber, may be 100 wt %. In a case where the water absorbent core contains the hydrophilic fiber, the core concentration is less than 100 wt %, preferably 10-wt %, more preferably 20-90 wt %, and still more preferably 25-80 wt %. In a case where the core concentration is less than 10 wt %, an amount of the water absorbent agent composition used is small, so that there is a possibility that a deodorizing function is not given sufficiently to the whole of a paper diaper. In a case where the core concentration is more than 90 wt %, an amount of the hydrophilic fiber used is small, so that there is a possibility that an effect yielded by use of the hydrophilic fiber is not obtained sufficiently.

[6] Absorbent Article

The present invention also provides an absorbent article for absorbing urine, which uses the aforementioned packaged water absorbent agent composition, a method for producing the absorbent article, and a method for storing or stocking the absorbent article.

"Absorbent article" of the present invention indicates an absorbent core which is intermediate consumer goods or end consumer goods for general consumers which use the absorbent core. Specifically, examples of the absorbent article include paper diapers, sanitary napkins, incontinence pads, pet sheets, litter, and the like. A preferable example of the absorbent article is an absorbent article for absorbing urine. A particularly preferable example of the absorbent article is a paper diaper.

To be more specific, the absorbent article (paper diaper, sanitary napkin, incontinence pad, pet sheet etc.) includes the absorbent core, a top sheet having liquid permeability, and a back sheet having liquid impermeability.

A method for producing the absorbent article in accordance with the present invention is not particularly limited. For example, the absorbent article may be produced in such a manner that an absorbent core prepared by blending the fiber base material and the water absorbent agent composition or causing the water absorbent agent composition to be sandwiched between the fiber base materials is further sandwiched between a liquid-permeable base material (top sheet) and a liquid-impermeable base material (back sheet), and providing the resultant with an elastic member, a diffusion layer, an adhesive tape etc. if necessary. Consequently, an absorbent article, particularly a paper diaper and a sanitary napkin, is produced.

The absorbent article thus produced is compressed and shaped so that a concentration of the absorbent core therein is 0.06-0.50 [g/cm$^3$], and a basic weight is 0.01-0.20 [g/cm$^2$].

The fiber base material is not particularly limited as long as it is hydrophilic fiber. Examples of the fiber base material include pulverized wood pulp, cotton linter, crosslinked cellulose fiber, rayon, cotton, wool, acetate fiber, vinylon, and the like, which are preferably air-laid.

Furthermore, the absorbent article can be stably stored or stocked in a packaged state for a long time, preferably for not less than 30 days, more preferably for not less than 60 days, and still more preferably for not less than 100 days (upper limit is 1,000 days or so) until the absorbent article is actually used, and can maintain an additional function for such a long time.

The water absorbent agent composition in accordance with the present invention can add an additional function (deodorizing function in particular) to the absorbent article, and carries out an excellent additional function (deodorizing function in particular) and an excellent absorbent property for a long time (not less than 30 days) until the absorbent article is actually used. Such an absorbent article is not particularly limited. Specific examples of such an absorbent article include sanitary materials such as paper diapers for adults, paper diapers for children, sanitary napkins, incontinence pads, and the like. In these applications, amounts of Re-Wet are small, resulting in strong feeling of dryness. Furthermore, since the absorbent article has a deodorizing function in particular, it is possible to greatly reduce a burden not only on a user who is wearing the absorbent article but also on persons who care the user (in case of paper diapers for adults). Furthermore, not only in use of a paper diaper but also in disposing of or storing a used paper diaper, offensive odor is less likely to be generated or increase. This makes it easy to dispose of the used paper diaper in homes and facilities, and reduces necessity of special equipment for disposal (e.g. airtight container, instant collection of garbage).

EXAMPLES

The following description will discuss in details the present invention with reference to Examples and Comparative Examples. Note, however, that the present invention is not limited to these Examples. For convenience, "liter" may be indicated as "L" and "weight %" may be indicated as "wt %". Unless otherwise specified, physical properties of water absorbent resin powder, water absorbent resin particles, a water absorbent agent composition, and an absorbent article which are obtained in the present invention were measured under conditions that a temperature was 25° C.±2° C. and a relative humidity was 50% RH.

(7) Methods for Measuring Physical Properties (7-1) Deodorizing Test a (Evaluation of Deodorizing Property of Water Absorbent Agent Composition)

50 ml was sampled from a mixture of human urine collected from 10 adults, and was poured into a 120 ml polypropylene vessel having a lid (product name: Pack-Ace, manufactured by Teraoka Co., Ltd.; size: 58 mm in bore diameter×54 mm in bottom diameter×74 mm in height). The human urine used was obtained within 2 hours from urination.

Subsequently, 2.0 g of a water absorbent agent composition was added to the polypropylene vessel containing 50 ml of the human urine, so that the water absorbent agent composition absorbed the human urine to be 25-times-swollen gel. Then, the vessel was covered with the lid and kept at 37° C.

At time points when 1 minute (initial stage), 3 hours, and 6 hours have elapsed from a time point when the water absorbent agent composition absorbed the human urine, i.e. when the swollen gel was formed, the lid of the vessel was removed, odor was smelled at a position approximately 3 cm above the opening of the vessel, and the deodorizing property of the water absorbent agent composition was evaluated in accordance with a standard below.

The deodorizing property was evaluated by 20 adult monitors who were selected arbitrarily. Determination of the deodorizing property was made in such a manner that every monitor made an evaluation based on five scales including "1: no smell", "2: hardly noticeable smell", "3: noticeable but sufferable smell", "4: sharp smell", and "5: overpowering smell", the "5" being an odor obtained when the test was made with only human urine without addition of the water absorbent agent composition, and the deodorizing property was determined based on an average of evaluations of all the monitors.

(7-2) Stabilization Index (Test on Stability in Maintaining Deodorizing Effect)

A test on stability in maintaining a deodorizing effect is a test to evaluate or expect a deodorizing ability of a water absorbent agent composition which is processed by a user to be a paper diaper etc. and then actually used by an end customer, compared to a deodorizing ability of the water absorbent agent composition immediately after production thereof (normally, at this point, quality control of physical properties, including a water absorbent property, of the water absorbent agent composition is made and only acceptable products are shipped). A stabilization index was obtained by carrying out an acceleration test below so as to evaluate a decrease in deodorizing ability of the water absorbent agent composition after production thereof (it was separately confirmed that other physical properties, including a water absorbent property, were not substantially changed).

Specifically, the acceleration test was carried out as follows. A targeted water absorbent agent composition was subjected to the deodorizing test A mentioned in the item (7-1) right after production of the water absorbent agent composition (within 3 days, preferably within 1 day, after the production), and a result of evaluation was Xa. The water absorbent agent composition and human urine used were in such amounts as to provide not less than 100 g of swollen gel.

Subsequently, a water absorbent agent composition which was the same as the water absorbent agent composition used in the deodorizing test A, i.e. 100 g of the water absorbent agent composition which was not swollen, was put in a 250 ml polyethylene vessel (reagent bottle manufactured by TOP; polypropylene wide-mouth bottle), and the polyethylene vessel was covered with a lid so as to be a water absorbent agent package. Then, the water absorbent agent package was left (stored) at a temperature of 40° C. for 30 days in an atmosphere of 75% RH in relative humidity. Then, the water absorbent agent composition taken out from the water absorbent agent package left for 30 days was subjected to the deodorizing test A which used human urine collected from the same 10 adults as those in the former deodorizing test A (whose physical conditions and dietary lives were the same as those in the former deodorizing test A) and which was monitored by the same 20 adults as in the former deodorizing test A. A result of the evaluation was Xb. The stabilization index of the deodorizing effect was calculated based on Equation (1) below and Xa and Xb obtained as above.

$$\text{Stabilization index } [\%] = (Xa/Xb) \times 100 \quad (1)$$

(7-3) Degradable Soluble Component

Initially, a pH electrode to be used in measurement of a degradable soluble component was calibrated with pH standard buffers (pH: 4.0, pH: 7.0, pH: 10.0).

Subsequently, 50 ml of a physiological saline solution (0.9 wt % aqueous solution of sodium chloride) which had been prepared beforehand was measured in a 100 ml glass beaker, and while the physiological saline solution was stirred with a stir bar (30 mm in length×8 mm in outer diameter), a 0.1 N aqueous solution of sodium hydroxide was titrated so that pH of the physiological saline solution became 10. An amount of titration here (Vab [ml]) was obtained as a blank. Subsequently, the physiological saline solution was stirred, 0.1 N aqueous solution of hydrochloric acid was titrated to the physiological saline solution so that pH of the physiological saline solution became 2.7. An amount of titration here (Vbb [ml]) was obtained as a blank, too.

On the other hand, L-ascorbic acid was added to a physiological saline solution which had been prepared beforehand so that a concentration of the L-ascorbic acid was 0.05 wt %, and thus a deterioration test solution was prepared. That is, 0.5 g of L-ascorbic acid was dissolved in 999.5 g of a physiological saline solution so as to prepare a 1000.0 g of a deterioration test solution.

Subsequently, 25 ml of the deterioration test solution was poured into a 250 ml polypropylene vessel with a lid, and then 1.0 g of a water absorbent agent composition was added to the polypropylene vessel, so that swollen gel was formed. Thereafter, the vessel was covered with the lid and sealed, and left at 37° C. for 16 hours.

After the above operation (after 16 hours), 175 ml of a physiological saline solution was poured into the polypropylene vessel and the resultant was stirred with a stir bar (30 mm in length×8 mm in outer diameter) at a stirring velocity of 500±50 rpm for 1 hour, so that an extractable content was extracted. Then, filtration was made by using a filter paper (manufactured by Toyo Roshi Kaisha, Ltd.; No. 2/retained particle diameter 5 μm (specified in JIS P 3801) so as to obtain a filtrate.

20 ml of the filtrate (recorded as F [ml]) obtained as a result of the above operation was measured in a 100 ml glass beaker, and a physiological saline solution was added to the filtrate so that the whole amount of the resultant was 50 ml, and the resultant was regarded as a titration liquid. In a case where the amount of the filtrate was less than 20 ml, the amount of the filtrate (F[ml]) was recorded and then a physiological saline solution was added to the filtrate so that the whole amount of the resultant was 50 ml, and the resultant was regarded as a titration liquid.

Subsequently, while the titration liquid was stirred with a stir bar (30 mm in length×8 mm in outer diameter), a 0.1 N aqueous solution of sodium hydroxide was titrated to the titration liquid so that pH of the titration liquid became 10. Then, the amount of titration here (Va [ml]) was obtained. Thereafter, while the titration liquid was stirred, a 0.1 N aqueous solution of hydrochloric acid was titrated to the titration liquid so that pH of the titration liquid became 2.7. Then, the amount of titration here (Vb [ml]) was obtained. Then, a degradable soluble component was calculated based on Equation (2) below and these amounts of titration.

$$\text{Degradable soluble component } [\text{wt } \%] = \{(Wa+Wb)/m)\} \times 100 \quad (2)$$

In the Equation (2), Wa [g] indicates a relative weight of a unit having an acid radical in the extractable contents of the water absorbent agent composition, and Wb [g] indicates a relative weight of a unit having a carboxyl group (carboxylate) neutralized with a basic substance in the extractable contents of the water absorbent agent composition. Wa [g] and Wb [g] can be obtained based on respective Equations (3) and (4) below.

$$Wa \text{ [g]} = Na \times 72 \times 200/F \quad (3)$$

$$Wb \text{ [g]} = Nb \times 94 \times 200/F \quad (4)$$

m [g] indicates a weight of the water absorbent agent composition.

"72" in the Equation (3) is a weight of a repeating unit per 1 mol of an acrylic acid polymer, and "94" in the Equation (4) is a weight of a repeating unit per 1 mol of a sodium acrylate. In a case where monomers having an acid radical other than acrylic acid are copolymerized or in a case where alkaline metal salt other than sodium salt, such as potassium salt, lithium salt etc., are used, the above "72" or "94" is appropriately converted into an average weight of a repeating unit per 1 mol containing the monomer or the alkaline metal salt.

Na [mol] in the Equation (3) indicates an amount by mole of an acid radical in extractable contents in the titration liquid (filtrate). Nb [mol] in the Equation (4) indicates an amount by mole of a carboxyl group (carboxylate) neutralized with a basic substance in the extractable contents in the titration liquid (filtrate). Na [mol] and Nb [mol] can be obtained based on respective Equations (5) and (6) below.

$$Na \text{ [mol]} = \{(Va-Vab)/1000\} \times 0.1 \quad (5)$$

$$Nb \text{ [mol]} = N_1 - Na \quad (6)$$

$N_1$ [mol] in the Equation (6) is the whole amount by mole of extractable contents in the titration liquid (filtrate), and can be obtained based on Equation (7) below.

$$N_1 \text{ [mol]} = \{(Vb-Vbb)/1000\} \times 0.1 \quad (7)$$

(7-4) Deodorizing Test B (Evaluation of Deodorizing Property of Absorbent Article)

(Preparation of Absorbent Article)

50 parts by weight of a water absorbent agent composition and 50 parts by weight of pulverized tree pulp were dry-mixed by use of a mixer. The resulting mixture was subjected to air-sheet forming by a batch-type air-sheet forming device on a wire screen of 400 meshes (mesh opening size was 38 μm) so that a web of 120 mm×400 mm in size was formed. Then, the web was pressed for 5 seconds with a pressure of 196.14 kPa, so that an absorbent core of approximately 0.047 [g/cm$^2$] in basic weight was obtained.

Subsequently, a back sheet (liquid-impermeable sheet) having a so-called leg gather made of liquid-impermeable polypropylene, the aforementioned absorbent core, and a top sheet (liquid-permeable sheet) made of liquid-permeable polypropylene were attached to each other in this order with use of a double-faced tape. Thereafter, two so-called tape zip fasteners were attached to the resultant, so that an absorbent article (i.e. paper diaper) was formed. The weight of the absorbent article was 46 g.

(Deodorizing Test B)

The absorbent article prepared by the above operation was cut into pieces of 10 cm×10 cm in size, and the pieces were put in a 250 ml polypropylene vessel having a lid (product name: Pack-Ace/manufactured by Teraoka Co., Ltd.; size: 58 mm in bore diameter×54 mm in bottom diameter×154 mm in height).

Then, 20 g of human urine collected from an adult was added to the polypropylene vessel and thereafter the vessel was covered with the lid and the whole vessel was kept at 37° C.

After 6 hours had elapsed from a time point when the absorbent article absorbed the human urine, the lid was removed from the vessel, and odor was smelled at a position approximately 3 cm above the opening of the vessel, and a deodorizing property of the absorbent article was evaluated based on a standard below.

The deodorizing property was evaluated by 20 adult monitors who were selected arbitrarily. Determination of the deodorizing property was made based on a standard which was odor obtained when the same operation was made with only human urine poured into the vessel without use of the absorbent article. Every monitor made an evaluation based on six scales including "0: no smell", "1: scarcely noticeable smell", "2: noticeable but sufferable smell", "3: easily noticeable smell", "4: sharp smell", and "5: overpowering smell", the "5" being the standard odor, and the deodorizing property was determined based on an average of evaluations of all the monitors.

(7-5) Determination of Natural Ingredient (Caffeine, Catechins)

Determination of a natural ingredient (caffeine, catechins in particular) in a water absorbent agent composition was made in accordance with a method for measuring remaining monomers which is specified in ERT410.2-02.

That is, 0.5 g of the water absorbent agent composition was added to 200 ml of a 0.9 wt % aqueous solution of sodium chloride, and the resultant was stirred for 2 hours at 500 rpm, so that an extract liquid was obtained. The extract liquid was analyzed with a high-performance liquid chromatography, the height or the area of a peak of each ingredient was compared with the height or the area of a peak of a standard material, so that the contained amount of the ingredient was obtained.

In an embodiment of the present invention, when the contained amounts of caffeine and catechins are 5 ppm to 1 wt % in total, it can be confirmed that the water absorbent agent composition contains an appropriate amount of the natural ingredient.

(7-6) Determination of Natural Ingredient (Tannin)

Determination of a natural ingredient (tannin) in the water absorbent agent composition was made by a Folin Ciocalteu method or a Folin Denis method.

That is, 0.5 g of the water absorbent agent composition was added to 200 ml of a 0.9 wt % aqueous solution of sodium chloride, and stirred at 500 rpm for 2 hours so as to obtain an extract liquid. The extract liquid was mixed with a Folin reagent and the degree of coloring by reduction was measured by absorption spectroscopy, so that the contained amount of a natural ingredient (tannin) in the water absorbent agent composition was obtained.

(7-7) Moisture Absorption Blocking Ratio (BR)

Approximately 2 g of the water absorbent agent composition was evenly sprayed in an aluminum cup of 52 mm in diameter, and then the aluminum cup was left for 1 hour in a constant temperature and constant humidity testing chamber (PLATINOUS LUCIFERPL-2G, manufactured by TABAI ESPEC) of 25° C. in temperature and 90±5% RH in relative humidity. After 1 hour, the water absorbent agent composition in the aluminum cup was softly moved onto a JIS standard sieve of JIS 8.6 meshes (mesh opening size was 2,000 μm) (The IIDA TESTING SIEVE: 80 mm in bore diameter), and classified with a Ro-Tap sieve shaker (manufactured by IIDA SEISAKUSHO, ES-65 sieve shaker; revolutions per minute: 230 rpm, taps per minute: 130 rpm) for 5 seconds, and the weight (Wc [g]) of the water absorbent agent composition remaining on the meshes and the weight (Wd [g]) of the water absorbent agent composition having passed through the meshes were measured. Then, a moisture absorption blocking ratio (BR) which is a fluidity index at moisture absorption was calculated in accordance with Equation (8) below.

$$BR \text{ [wt \%]} = \{Wc/(Wc+Wd)\} \times 100 \quad (8)$$

(7-9) Measurement of Amount of Iron (Fe)

An amount of Fe (Fe content) was obtained by an ICP (Inductively Coupled Plasma) method in accordance with an analytical curve prepared based on a standard solution.

Production Example 1

4.00 g of polyethylene glycol diacrylate (average amount by mole of ethylene oxide to be added was 8) as an internal crosslinking agent was dissolved in 5,500 g of a sodium acrylate aqueous solution whose neutralization rate was 75 mol % (a monomer concentration was 33 wt %) so that an aqueous monomer solution (1) was obtained, and then the aqueous monomer solution (1) was deaerated under nitrogen gas atmosphere for 30 min.

Subsequently, the aqueous monomer solution (1) was poured into a reaction container formed by providing a lid to a 10 L stainless double-arm kneader equipped with two sigma vanes and a jacket, and nitrogen gas was injected into the reaction container while keeping a temperature of the reaction solution at 30° C., so as to carry out replacement with nitrogen in the system.

While the aqueous monomer solution (1) was stirred, 2.46 g of sodium persulfate and 0.10 g of L-ascorbic acid each of which serves as a polymerization initiator were separately added to the aqueous monomer solution (1) so that polymerization was started. The polymerization was started approximately 1 min after addition of the polymerization initiator.

A resulting hydrous gelatinous crosslinking polymer (1) was polymerized at 30-80° C. while it was crushed, and the hydrous gelatinous crosslinking polymer (1) was taken out after 60 min had elapsed from start of the polymerization. The resulting hydrous gelatinous crosslinking polymer (1) was finely crushed into particles of approximately not more than 5 mm in diameter.

Next, the hydrous gelatinous crosslinking polymer (1) thus crushed finely was spread on a wire sheet whose mesh opening size was 300 μm (50 meshes), and was dried with hot air at 180° C. for 40 min. Then, the resultant was pulverized with a vibrating mill and was further classified and prepared with a JIS standard sieve of 850 μm in mesh opening size. Through a series of these operations, water absorbent resin powder (1) having a non-uniformly pulverized shape and a weight average particle diameter (D50) of 295 μm was obtained.

Then, a surface-crosslinking agent solution containing 0.05 parts by weight of ethyleneglycol diglycidyl ether, 1 part by weight of propylene glycol, 3 parts by weight of water, and 1 part by weight of isopropyl alcohol was evenly mixed with 100 parts by weight of the water absorbent resin powder (1), and the resultant was subjected to a heat treatment at 210° C. for 50 min, so that surface-crosslinked water absorbent resin particles (1) were obtained. The water absorbent resin particles (1) thus obtained had a moisture content of 1 wt %, a CRC of 39 [g/g], an AAP of 28 [g/g], a weight average particle diameter (D50) of 320 μm, and particles, which are not less than 300 μm, of 61 wt %. An amount of Fe in a 48% aqueous solution of sodium hydroxide used for obtaining a sodium acrylate aqueous solution whose neutralization rate was 75 mol % was 0.4 ppm.

Production Example 2

The same operation as that in Production Example 1 was carried out except that the monomer concentration was changed to 38 wt %, the internal crosslinking agent was changed to 7.0 g of trimethylolpropane triacrylate, and a pulverizing condition of the vibrating mill was appropriately changed, so that water absorbent resin powder (2) having a non-uniformly pulverized shape and a weight average particle diameter (D50) of 360 μm was obtained.

Subsequently, the same surface crosslinking agent solution as that in Production Example 1 was evenly mixed with the water absorbent resin powder (2), and the resultant was subjected to a heat treatment at 210° C. for 45 min, so that surface-crosslinked water absorbent resin particles (2) were obtained. The water absorbent resin particles (2) thus obtained had a moisture content of 1 wt %, a CRC of 34 [g/g], an AAP of 31 [g/g], a weight average particle size diameter (D50) of 370 μm, and particles, which are not less than 300 μm, of 73 wt %.

Example 1

To the water absorbent resin particles (1) obtained in Production Example 1, 5.0 wt % of a green tea extract as a natural ingredient, 100 ppm of propyl gallate as a temporal deterioration preventing agent, and 0.025 wt % of a 45 wt % aqueous solution of diethylenetriaminepentaacetic acid pentasodium as a chelating agent were added in a form of a mixture solution (so as to be contained in these amounts). Then, the resultant was mixed with use of a screw type mixer under conditions that the number of revolution of the mixer was 350 rpm, a temperature of the powder was 60° C., and a time for mixing was 1 min, so that a water absorbent agent composition (1) was obtained. In Examples and Comparative Examples which will be mentioned later, the mixing was carried out under the same conditions unless otherwise specified.

The green tea extract used was an aqueous solution obtained by pulverizing 50 g of generally commercially available green tea into particles which can pass through a standard sieve of 500 μm, and then putting the particles in 500 g of hot water at approximately 80° C. and extracting an aqueous solution while stirring the particles for 1 hour, and further filtering the aqueous solution.

The results of the deodorizing test A on the resulting water absorbent agent composition (1), a stabilization index and a degradable soluble component in the test on stability in maintaining a deodorizing effect of the resulting water absorbent agent composition (1), and the deodorizing test B on an absorbent article (1) are shown in Table 1 (and Tables 3, 5, and 6). A total contained amount of caffeine and catechins in the water absorbent agent composition (1) was 0.3 wt %. Furthermore, the result of measuring an amount of Fe in the resulting water absorbent agent composition (1) is shown in Table 6. An AAP of the water absorbent agent composition (1) was 26 [g/g]

Example 2

To the water absorbent resin particles (1) obtained in Production Example 1, 10.0 wt % of a green tea extract as a natural ingredient, 50 ppm of sodium erythorbate as a temporal deterioration preventing agent, and 0.025 wt % of a 45 wt % aqueous solution of diethylenetriaminepentaacetic acid pentasodium as a chelating agent were added in a form of a mixture solution (so as to be contained in these amounts). Then, the resultant was mixed so that a water absorbent agent composition (2) was obtained. The green tea extract used was an aqueous solution obtained through the same operation as in Example 1.

The results of the deodorizing test A on the resulting water absorbent agent composition (2), a stabilization index and a degradable soluble component in the test on stability in maintaining a deodorizing effect of the resulting water absorbent agent composition (2), and the deodorizing test B on an absorbent article (2) are shown in Table 1. A total contained amount of caffeine and catechins in the water absorbent agent composition (2) was 0.65 wt %.

Example 3

To the water absorbent resin particles (2) obtained in Production Example 2, 0.3 wt % of an oolong tea extract as a natural ingredient, 10 ppm of propyl gallate as a temporal deterioration preventing agent, and 0.025 wt % of a 45 wt % aqueous solution of diethylenetriaminepentaacetic acid pentasodium as a chelating agent were added in a form of a mixture solution (so as to be contained in these amounts). Then, the resultant was mixed so that a water absorbent agent composition (3) was obtained. The oolong tea extract used was an aqueous solution obtained by pulverizing 50 g of generally commercially available oolong tea into particles which can pass through a standard sieve of 500 μm, and then putting the particles in 500 g of hot water at approximately 80° C. and extracting an aqueous solution while stirring the particles for 1 hour, and further filtering the aqueous solution.

The results of the deodorizing test A on the resulting water absorbent agent composition (3), a stabilization index and a degradable soluble component in the test on stability in maintaining a deodorizing effect of the resulting water absorbent agent composition (3), and the deodorizing test B on an absorbent article (3) are shown in Table 1.

Example 4

To the water absorbent resin particles (2) obtained in Production Example 2, 0.5 wt % of a black tea extract as a natural ingredient, 30 ppm of sodium erythorbate as a temporal deterioration preventing agent, and 0.025 wt % of a 45 wt % aqueous solution of diethylenetriaminepentaacetic acid pentasodium as a chelating agent were added in a form of a mixture solution (so as to be contained in these amounts). Then, the resultant was mixed so that a water absorbent agent composition (4) was obtained. The black tea extract used was an aqueous solution obtained by pulverizing 50 g of generally commercially available black tea into particles which can pass through a standard sieve of 500 μm, and then putting the particles in 500 g of hot water at approximately 80° C. and extracting an aqueous solution while stirring the particles for 1 hour, and further filtering the aqueous solution.

The results of the deodorizing test A on the resulting water absorbent agent composition (4), a stabilization index and a degradable soluble component in the test on stability in maintaining a deodorizing effect of the resulting water absorbent agent composition (4), and the deodorizing test B on an absorbent article (4) are shown in Table 1. A total contained amount of caffeine and catechins in the water absorbent agent composition (4) was 0.04 wt %.

Example 5

To the water absorbent resin particles (2) obtained in Production Example 2, 3.0 wt % of an oolong tea extract as a natural ingredient, 50 ppm of sodium erythorbate as a temporal deterioration preventing agent, 0.025 wt % of a 45 wt % aqueous solution of diethylenetriaminepentaacetic acid pentasodium as a chelating agent, and 7.0 wt % of water were added in a form of a mixture solution (so as to be contained in these amounts). Then, the resultant was mixed so that a water absorbent agent composition (5) was obtained. The oolong tea extract used was an aqueous solution obtained through the same operation as in Example 3.

The results of the deodorizing test A on the resulting water absorbent agent composition (5), a stabilization index and a degradable soluble component in the test on stability in maintaining a deodorizing effect of the resulting water absorbent agent composition (5), and the deodorizing test B on an absorbent article (5) are shown in Table 1 (and Table 4). A contained amount of tannin was 0.8 wt %. A moisture absorption blocking ratio (BR) of the water absorbent agent composition (5) was 100 wt %.

Example 6

To the water absorbent resin particles (1) obtained in Production Example 1, 1.0 wt % of a green tea extract as a natural ingredient, 100 ppm of sodium hypochlorite as a temporal deterioration preventing agent, 0.025 wt % of a 45 wt % aqueous solution of diethylenetriaminepentaacetic acid pentasodium as a chelating agent, and 1.0 wt % of water were added in a form of a mixture solution (so as to be contained in these amounts). Then, the resultant was mixed so that a water absorbent agent composition (6) was obtained. The green tea extract used was an aqueous solution obtained through the same operation as in Example 1.

The results of the deodorizing test A on the resulting water absorbent agent composition (6), a stabilization index and a degradable soluble component in the test on stability in maintaining a deodorizing effect of the resulting water absorbent agent composition (6), and the deodorizing test B on an absorbent article (6) are shown in Table 1.

Example 7

To the water absorbent resin particles (1) obtained in Production Example 1, 3.0 wt % of an oolong tea extract as a natural ingredient, 5 ppm of potassium hypochlorite as a temporal deterioration preventing agent, 0.025 wt % of a 45 wt % aqueous solution of diethylenetriaminepentaacetic acid pentasodium as a chelating agent, and 7.0 wt % of water were added in a form of a mixture solution (so as to be contained in these amounts). Then, the resultant was mixed so that a water absorbent agent composition (7) was obtained. The oolong tea extract used was an aqueous solution obtained through the same operation as in Example 3.

The results of the deodorizing test A on the resulting water absorbent agent composition (7), a stabilization index and a degradable soluble component in the test on stability in maintaining a deodorizing effect of the resulting water absorbent agent composition (7), and the deodorizing test B on an absorbent article (7) are shown in Table 1. A total contained amount of caffeine and catechins in the water absorbent agent composition (7) was 0.17 wt %.

Example 8

To the water absorbent resin particles (1) obtained in Production Example 1, 0.05 wt % of a pu-erh tea extract as a natural ingredient, 10 ppm of sodium benzoate as a temporal deterioration preventing agent, and 0.025 wt % of a 45 wt % aqueous solution of diethylenetriaminepentaacetic acid pentasodium as a chelating agent were added in a form of a mixture solution (so as to be contained in these amounts). Then, the resultant was mixed so that a water absorbent agent composition (8) was obtained. The pu-erh tea extract used was an aqueous solution obtained by pulverizing 50 g of generally commercially available pu-erh tea into particles which can pass through a standard sieve of 500 μm, and then putting the particles in 500 g of hot water at approximately 80° C. and extracting an aqueous solution while stirring the particles for 1 hour, and further filtering the aqueous solution.

The results of the deodorizing test A on the resulting water absorbent agent composition (8), a stabilization index and a degradable soluble component in the test on stability in maintaining a deodorizing effect of the resulting water absorbent agent composition (8), and the deodorizing test B on an absorbent article (8) are shown in Table 1.

Example 9

To the water absorbent resin particles (1) obtained in Production Example 1, 0.3 wt % of an oolong tea extract as a natural ingredient, 100 ppm of potassium sorbate as a temporal deterioration preventing agent, and 0.025 wt % of a 45 wt % aqueous solution of diethylenetriaminepentaacetic acid pentasodium as a chelating agent were added in a form of a mixture solution (so as to be contained in these amounts). Then, the resultant was mixed so that a water absorbent agent composition (9) was obtained. The oolong tea extract used was an aqueous solution obtained through the same operation as in Example 3.

The results of the deodorizing test A on the resulting water absorbent agent composition (9), a stabilization index and a degradable soluble component in the test on stability in maintaining a deodorizing effect of the resulting water absorbent agent composition (9), and the deodorizing test B on an absorbent article (9) are shown in Table 1.

Example 10

To the water absorbent resin particles (1) obtained in Production Example 1, 0.15 wt % of an extract from Theaceae plant leaves as a natural ingredient, 1 ppm of methylparaben as a temporal deterioration preventing agent, 0.025 wt % of a 45 wt % aqueous solution of diethylenetriaminepentaacetic acid pentasodium as a chelating agent, and 0.85 wt % of water were added in a form of a mixture solution (so as to be contained in these amounts). Then, the resultant was mixed so that a water absorbent agent composition (10) was obtained.

The results of the deodorizing test A on the resulting water absorbent agent composition (10), a stabilization index and a degradable soluble component in the test on stability in maintaining a deodorizing effect of the resulting water absorbent agent composition (10), and the deodorizing test B on an absorbent article (10) are shown in Table 1. A total contained amount of caffeine and catechins in the water absorbent agent composition (10) was 0.075 wt %.

Example 11

To the water absorbent resin particles (1) obtained in Production Example 1, 0.015 wt % of an extract from Theaceae plant leaves as a natural ingredient, 0.1 ppm of propylparaben as a temporal deterioration preventing agent, 0.025 wt % of a 45 wt % aqueous solution of diethylenetriaminepentaacetic acid pentasodium as a chelating agent, and 0.085 wt % of water were added in a form of a mixture solution (so as to be contained in these amounts). Then, the resultant was mixed so that a water absorbent agent composition (11) was obtained.

The results of the deodorizing test A on the resulting water absorbent agent composition (11), a stabilization index and a degradable soluble component in the test on stability in maintaining a deodorizing effect of the resulting water absorbent agent composition (11), and the deodorizing test B on an absorbent article (11) are shown in Table 1 (and Tables 3 and 5). A total contained amount of caffeine and catechins in the water absorbent agent composition (11) was 0.008 wt %. An AAP of the water absorbent agent composition (11) was 26 [g/g].

Example 12

To the water absorbent resin particles (2) obtained in Production Example 2, 0.25 wt % of a black tea extract as a natural ingredient, 10 ppm of biphenyl as a temporal deterioration preventing agent, and 0.025 wt % of a 45 wt % aqueous solution of diethylenetriaminepentaacetic acid pentasodium as a chelating agent were added in a form of a mixture solution (so as to be contained in these amounts). Then, the resultant was mixed so that a water absorbent agent composition (12) was obtained. The black tea extract used was an aqueous solution obtained through the same operation as in Example 4.

The results of the deodorizing test A on the resulting water absorbent agent composition (12), a stabilization index and a degradable soluble component in the test on stability in maintaining a deodorizing effect of the resulting water absorbent agent composition (12), and the deodorizing test B on an absorbent article (12) are shown in Table 1.

Example 13

To the water absorbent resin particles (2) obtained in Production Example 2, 0.5 wt % of a black tea extract as a natural ingredient, 50 ppm of orthophenylphenol as a temporal deterioration preventing agent, and 0.025 wt % of a 45 wt % aqueous solution of diethylenetriaminepentaacetic acid pentasodium as a chelating agent were added in a form of a mixture solution (so as to be contained in these amounts). Then, the resultant was mixed so that a water absorbent agent composition (13) was obtained. The black tea extract used was an aqueous solution obtained through the same operation as in Example 4.

The results of the deodorizing test A on the resulting water absorbent agent composition (13), a stabilization index and a degradable soluble component in the test on stability in maintaining a deodorizing effect of the resulting water absorbent agent composition (13), and the deodorizing test B on an absorbent article (13) are shown in Table 1. A contained amount of tannin was 0.11 wt %.

Example 14

To the water absorbent resin particles (1) obtained in Production Example 1, 3.0 wt % of an oolong tea extract as a natural ingredient, 5 ppm of butylparaben as a temporal deterioration preventing agent, 0.025 wt % of a 45 wt % aqueous solution of diethylenetriaminepentaacetic acid pentasodium as a chelating agent, and 7.0 wt % of water were added in a form of a mixture solution (so as to be contained in these amounts). Then, the resultant was mixed so that a water absorbent agent composition (14) was obtained. The oolong tea extract used was an aqueous solution obtained through the same operation as in Example 3.

The results of the deodorizing test A on the resulting water absorbent agent composition (14), a stabilization index and a degradable soluble component in the test on stability in maintaining a deodorizing effect of the resulting water absorbent agent composition (14), and the deodorizing test B on an absorbent article (14) are shown in Table 1.

Example 15

To the water absorbent resin particles (2) obtained in Production Example 2, 0.25 wt % of a black tea extract as a natural ingredient, 10 ppm of butylparaben as a temporal deterioration preventing agent, and 0.025 wt % of a 45 wt % aqueous solution of diethylenetriaminepentaacetic acid pentasodium as a chelating agent were added in a form of a mixture solution (so as to be contained in these amounts). Then, the resultant was mixed so that a water absorbent agent composition (15) was obtained. The black tea extract used was an aqueous solution obtained through the same operation as in Example 4.

The results of the deodorizing test A on the resulting water absorbent agent composition (15), a stabilization index and a degradable soluble component in the test on stability in maintaining a deodorizing effect of the resulting water absorbent agent composition (15), and the deodorizing test B on an absorbent article (15) are shown in Table 1.

Example 16

To the water absorbent resin particles (2) obtained in Production Example 2, 0.1 wt % of an extract from Fagaceae plant leaves as a natural ingredient, 20 ppm of sodium benzoate as a temporal deterioration preventing agent, 0.025 wt % of a 45 wt % aqueous solution of diethylenetriaminepentaacetic acid pentasodium as a chelating agent, and 0.9 wt % of water were added in a form of a mixture solution (so as to be contained in these amounts). Then, the resultant was mixed so that a water absorbent agent composition (16) was obtained.

The results of the deodorizing test A on the resulting water absorbent agent composition (16), a stabilization index and a degradable soluble component in the test on stability in maintaining a deodorizing effect of the resulting water absorbent agent composition (16), and the deodorizing test B on an absorbent article (16) are shown in Table 1. A contained amount of tannin was 0.065 wt %.

Example 17

To the water absorbent resin particles (2) obtained in Production Example 2, 0.03 wt % of an extract from Fagaceae plant leaves as a natural ingredient, 10 ppm of sodium benzoate as a temporal deterioration preventing agent, 0.025 wt % of a 45 wt % aqueous solution of diethylenetriaminepentaacetic acid pentasodium as a chelating agent, and 0.97 wt % of water were added in a form of a mixture solution (so as to be contained in these amounts). Then, the resultant was mixed so that a water absorbent agent composition (17) was obtained.

The results of the deodorizing test A on the resulting water absorbent agent composition (17), a stabilization index and a degradable soluble component in the test on stability in maintaining a deodorizing effect of the resulting water absorbent agent composition (17), and the deodorizing test B on an absorbent article (17) are shown in Table 1.

Example 18

To the water absorbent resin particles (2) obtained in Production Example 2, 0.0050 wt % of a pu-erh tea extract as a natural ingredient, 30 ppm of sodium benzoate as a temporal deterioration preventing agent, 0.025 wt % of a 45 wt % aqueous solution of diethylenetriaminepentaacetic acid pentasodium as a chelating agent, and 1.0 wt % of water were added in a form of a mixture solution (so as to be contained in these amounts). Then, the resultant was mixed so that a water absorbent agent composition (18) was obtained. The pu-erh tea extract used was an aqueous solution obtained through the same operation as in Example 8.

The results of the deodorizing test A on the resulting water absorbent agent composition (18), a stabilization index and a degradable soluble component in the test on stability in maintaining a deodorizing effect of the resulting water absorbent agent composition (18), and the deodorizing test B on an absorbent article (18) are shown in Table 1.

Example 19

To the water absorbent resin particles (2) obtained in Production Example 2, 0.0001 wt % of a pu-erh tea extract as a natural ingredient, 50 ppm of propyl gallate as a temporal deterioration preventing agent, 0.025 wt % of a 45 wt % aqueous solution of diethylenetriaminepentaacetic acid pentasodium as a chelating agent, and 1.0 wt % of water were added in a form of a mixture solution (so as to be contained in these amounts). Then, the resultant was mixed so that a water absorbent agent composition (19) was obtained. The pu-erh tea extract used was an aqueous solution obtained through the same operation as in Example 8.

The results of the deodorizing test A on the resulting water absorbent agent composition (19), a stabilization index and a degradable soluble component in the test on stability in maintaining a deodorizing effect of the resulting water absorbent agent composition (19), and the deodorizing test B on an absorbent article (19) are shown in Table 1.

Example 20

To the water absorbent resin particles (1) obtained in Production Example 1, 0.1 wt % of a pu-erh tea extract as a natural ingredient, 0.01 ppm of sodium benzoate as a temporal deterioration preventing agent, 0.025 wt % of a 45 wt % aqueous solution of diethylenetriaminepentaacetic acid pentasodium as a chelating agent, and 1.0 wt % of water were added in a form of a mixture solution (so as to be contained in these amounts). Then, the resultant was mixed so that a water absorbent agent composition (20) was obtained. The pu-erh tea extract used was an aqueous solution obtained through the same operation as in Example 8.

The results of the deodorizing test A on the resulting water absorbent agent composition (20), a stabilization index and a degradable soluble component in the test on stability in maintaining a deodorizing effect of the resulting water absorbent agent composition (20), and the deodorizing test B on an absorbent article (20) are shown in Table 1.

Comparative Example 1

The water absorbent resin particles (1) obtained in Production Example 1 were regarded as a comparative water absorbent agent composition (1).

The results of the deodorizing test A on the resulting comparative water absorbent agent composition (1), a stabilization index and a degradable soluble component in the test on stability in maintaining a deodorizing effect of the resulting comparative water absorbent agent composition (1), and the deodorizing test B on a comparative absorbent article (1) are shown in Table 2.

Comparative Example 2

To the water absorbent resin particles (1) obtained in Production Example 1, 50 ppm of propyl gallate as a temporal deterioration preventing agent and 0.025 wt % of a 45 wt % aqueous solution of diethylenetriaminepentaacetic acid pentasodium as a chelating agent were added in a form of a mixture solution (so as to be contained in these amounts). Then, the resultant was mixed so that a comparative water absorbent agent composition (2) was obtained.

The results of the deodorizing test A on the resulting comparative water absorbent agent composition (2), a stabilization index and a degradable soluble component in the test on stability in maintaining a deodorizing effect of the resulting comparative water absorbent agent composition (2), and the deodorizing test B on a comparative absorbent article (2) are shown in Table 2.

Comparative Example 3

To the water absorbent resin particles (1) obtained in Production Example 1, 30 ppm of sodium benzoate as a temporal deterioration preventing agent and 0.025 wt % of a 45 wt % aqueous solution of diethylenetriaminepentaacetic acid pentasodium as a chelating agent were added in a form of a mixture solution (so as to be contained in these amounts). Then, the resultant was mixed so that a comparative water absorbent agent composition (3) was obtained.

The results of the deodorizing test A on the resulting comparative water absorbent agent composition (3), a stabilization index and a degradable soluble component in the test on stability in maintaining a deodorizing effect of the resulting comparative water absorbent agent composition (3), and the deodorizing test B on a comparative absorbent article (3) are shown in Table 2.

Comparative Example 4

To the water absorbent resin particles (1) obtained in Production Example 1, 100 ppm of potassium sorbate as a temporal deterioration preventing agent and 0.025 wt % of a 45 wt % aqueous solution of diethylenetriaminepentaacetic acid pentasodium as a chelating agent were added in a form of a mixture solution (so as to be contained in these amounts). Then, the resultant was mixed so that a comparative water absorbent agent composition (4) was obtained.

The results of the deodorizing test A on the resulting comparative water absorbent agent composition (4), a stabilization index and a degradable soluble component in the test on stability in maintaining a deodorizing effect of the resulting comparative water absorbent agent composition (4), and the deodorizing test B on a comparative absorbent article (4) are shown in Table 2.

Comparative Example 5

To the water absorbent resin particles (1) obtained in Production Example 1, 0.5 wt % of a green tea extract as a natural ingredient was added, and then the resultant was mixed so that a comparative water absorbent agent composition (5) was obtained. The green tea extract used was an aqueous solution obtained through the same operation as in Example 1.

The results of the deodorizing test A on the resulting comparative water absorbent agent composition (5), a stabilization index and a degradable soluble component in the test on stability in maintaining a deodorizing effect of the resulting comparative water absorbent agent composition (5), and the deodorizing test B on a comparative absorbent article (5) are shown in Table 2.

Comparative Example 6

To the water absorbent resin particles (1) obtained in Production Example 1, 0.1 wt % of a green tea extract as a natural ingredient was added, and then the resultant was mixed so that a comparative water absorbent agent composition (6) was obtained. The green tea extract used was an aqueous solution obtained through the same operation as in Example 1.

The results of the deodorizing test A on the resulting comparative water absorbent agent composition (6), a stabilization index and a degradable soluble component in the test on stability in maintaining a deodorizing effect of the resulting comparative water absorbent agent composition (6), and the deodorizing test B on a comparative absorbent article (6) are shown in Table 2.

Comparative Example 7

To the water absorbent resin particles (1) obtained in Production Example 1, 5.0 wt % of a black tea extract as a natural ingredient was added, and then the resultant was mixed so that a comparative water absorbent agent composition (7) was obtained. The black tea extract used was an aqueous solution obtained through the same operation as in Example 4.

The results of the deodorizing test A on the resulting comparative water absorbent agent composition (7), a stabilization index and a degradable soluble component in the test on stability in maintaining a deodorizing effect of the resulting comparative water absorbent agent composition (7), and the deodorizing test B on a comparative absorbent article (7) are shown in Table 2.

TABLE 1

"Ex." stands for "Example".

| | Water absorbent resin particles | Natural ingredient Kind (extract) | Added amount [wt %] | Temporal deterioration preventing agent kind | Added amount [ppm] | Water [wt %] | Temporal deterioration preventing agent/ natural ingredient [—] | Water Absorbent agent composition | Deodorizing test A | Stabilization index [%] | Degradable soluble component [wt %] | Absorbent article Deodorizing test B |
|---|---|---|---|---|---|---|---|---|---|---|---|---|
| Ex. 1 | (1) | Green tea | 5.0 | propyl gallate | 100 | — | 0.0020 | (1) | 2.5 | 100 | 18 | 2.9 |
| Ex. 2 | (1) | Green tea | 10.0 | sodium erythorbate | 50 | — | 0.0005 | (2) | 2.4 | 100 | 22 | 2.7 |
| Ex. 3 | (2) | Oolong tea | 0.3 | propyl gallate | 10 | — | 0.0033 | (3) | 2.5 | 96 | 27 | 2.8 |
| Ex. 4 | (2) | Black tea | 0.5 | sodium erythorbate | 30 | — | 0.0060 | (4) | 2.4 | 96 | 20 | 2.7 |
| Ex. 5 | (2) | Oolong tea | 3.0 | sodium erythorbate | 50 | 7.0 | 0.0017 | (5) | 2.3 | 100 | 21 | 2.6 |
| Ex. 6 | (1) | Green tea | 1.0 | sodium hypochlorite | 100 | 1.0 | 0.0100 | (6) | 2.4 | 96 | 20 | 2.6 |
| Ex. 7 | (1) | Oolong tea | 3.0 | potassium hypochlorite | 5 | 7.0 | 0.0002 | (7) | 2.3 | 92 | 33 | 2.9 |
| Ex. 8 | (1) | Pu-erh tea | 0.05 | sodium benzoate | 10 | — | 0.0200 | (8) | 2.6 | 100 | 31 | 3.0 |
| Ex. 9 | (1) | Oolong tea | 0.3 | potassium sorbate | 100 | — | 0.0333 | (9) | 2.4 | 100 | 19 | 2.7 |
| Ex. 10 | (1) | Theaceae plant | 0.15 | methylparaben | 1 | 0.85 | 0.0007 | (10) | 2.7 | 96 | 25 | 2.6 |

TABLE 1-continued

"Ex." stands for "Example".

| | Water absorbent resin particles | Natural ingredient Kind (extract) | Natural ingredient Added amount [wt %] | Temporal deterioration preventing agent kind | Temporal deterioration preventing agent Added amount [ppm] | Water [wt %] | Temporal deterioration preventing agent / natural ingredient [—] | Water Absorbent agent composition | Deodorizing test A | Stabilization index [%] | Degradable soluble component [wt %] | Absorbent article Deodorizing test B |
|---|---|---|---|---|---|---|---|---|---|---|---|---|
| Ex. 11 | (1) | Theaceae plant leaves | 0.015 | propylparaben | 0.1 | 0.085 | 0.0007 | (11) | 2.9 | 97 | 26 | 2.8 |
| Ex. 12 | (2) | Black tea | 0.25 | biphenyl | 10 | — | 0.0040 | (12) | 2.4 | 96 | 27 | 2.6 |
| Ex. 13 | (2) | Black tea | 0.5 | orthophenylphenol | 50 | — | 0.0100 | (13) | 2.4 | 100 | 24 | 2.6 |
| Ex. 14 | (1) | Oolong tea | 3.0 | butylparaben | 5 | 7.0 | 0.0002 | (14) | 2.3 | 96 | 33 | 2.9 |
| Ex. 15 | (2) | Black tea | 0.25 | butylparaben | 10 | — | 0.0040 | (15) | 2.4 | 100 | 27 | 2.7 |
| Ex. 16 | (2) | Fagaceae plant leaves | 0.1 | sodium benzoate | 20 | 0.9 | 0.0200 | (16) | 2.6 | 96 | 23 | 2.6 |
| Ex. 17 | (2) | Fagaceae plant leaves | 0.03 | sodium benzoate | 10 | 0.97 | 0.0333 | (17) | 2.8 | 97 | 25 | 2.8 |
| Ex. 18 | (2) | Pu-erh tea | 0.0050 | sodium benzoate | 30 | 1.0 | 0.6000 | (18) | 3.5 | 95 | 23 | 3.9 |
| Ex. 19 | (2) | Pu-erh tea | 0.0001 | propyl gallate | 50 | 1.0 | 50.0000 | (19) | 4.0 | 100 | 22 | 4.5 |
| Ex. 20 | (1) | Pu-erh tea | 0.1 | sodium benzoate | 0.01 | 1.0 | 0.00001 | (20) | 2.7 | 73 | 43 | 2.7 |

Although not described in Table 1, among the water absorbent agent compositions obtained in Examples 1-20, the water absorbent agent composition obtained by using the water absorbent resin particles (1) had a moisture content of 2-10 wt %, a CRC of 38-39 [g/g], an AAP of 26-28 [g/g], a weight average particle diameter (D50) of 320-330 μm, and particles, which are not less than 300 μm, of 61-wt %, and the water absorbent agent composition obtained by using the water absorbent resin particles (2) had a moisture content of 2-10 wt %, a CRC of 34-35 [g/g], an AAP of 29-30 [g/g], a weight average particle diameter (D50) of 380-390 μm, and particles, which are not less than 300 μm, of 75-78 wt %. Physical properties of the water absorbent agent compositions other than the deodorizing property did not show any substantial changes when those physical properties were measured again after 30 days storage of the water absorbent agent compositions.

TABLE 2

"Com. Ex." stands for "Comparative Example".

| | Water absorbent resin particles | Natural ingredient Kind (extract) | Natural ingredient Added amount [wt %] | Temporal deterioration preventing agent kind | Temporal deterioration preventing agent Added amount [ppm] | Water [wt %] | Comparative water absorbent agent composition | Deodorizing test A | Stabilization index [%] | Degradable soluble component [wt %] | Comparative absorbent article Deodorizing test B |
|---|---|---|---|---|---|---|---|---|---|---|---|
| Com. Ex. 1 | (1) | — | — | — | — | — | (1) | 4.0 | 89 | 51 | 4.7 |
| Com. Ex. 2 | (1) | — | — | propyl gallate | 50 | — | (2) | 4.0 | 98 | 23 | 4.8 |
| Com. Ex. 3 | (1) | — | — | sodium benzoate | 30 | — | (3) | 4.1 | 100 | 23 | 4.5 |
| Com. Ex. 4 | (1) | — | — | potassium sorbate | 100 | — | (4) | 4.0 | 93 | 21 | 4.7 |
| Com. Ex. 5 | (1) | Green tea | 0.5 | — | — | — | (5) | 2.5 | 69 | 50 | 2.7 |
| Com. Ex. 6 | (1) | Green tea | 0.1 | — | — | — | (6) | 2.7 | 73 | 53 | 2.8 |
| Com. Ex. 7 | (1) | Black tea | 5.0 | — | — | — | (7) | 2.5 | 63 | 45 | 2.8 |

SUMMARY

Comparison of Examples 1-20 and Comparative Examples 1-7 shows that use of the natural ingredient and the temporal deterioration preventing agent in combination allows an improvement in deodorizing performance and a reduction in degradable soluble component. Furthermore, comparison of Examples 1-17 and Examples 18-20 shows more preferable amounts of use of the natural ingredient and the temporal deterioration preventing agent and a more preferable ratio between the natural ingredient and the temporal deterioration preventing agent.

Example 21

To the water absorbent resin particles (1) obtained in Production Example 1, 5.0 wt % of a green tea extract as a natural ingredient, 100 ppm of propyl gallate as a temporal deterioration preventing agent, 0.5 wt % of propylene glycol as a hydrophilic organic solvent, and 0.025 wt % of a 45 wt % aqueous solution of diethylenetriaminepentaacetic acid pentasodium as a chelating agent were added in a form of a mixture solution (so as to be contained in these amounts). Then, the resultant was mixed so that a water absorbent agent composition (21) was obtained. The green tea extract used was an aqueous solution obtained through the same operation as in Example 1.

The results of the deodorizing test A on the resulting water absorbent agent composition (21), a stabilization index, a degradable soluble component, and an AAP in the test on stability in maintaining a deodorizing effect of the resulting water absorbent agent composition (21), and the deodorizing test B on an absorbent article (21) are shown in Table 3 (and Table 4). A moisture absorption blocking ratio (BR) of the water absorbent agent composition (21) was 100 wt %.

Example 22

To the water absorbent resin particles (1) obtained in Production Example 1, 0.015 wt % of an extract from Theaceae plant leaves as a natural ingredient, 0.1 ppm of propylparaben as a temporal deterioration preventing agent, 0.085 wt % of water, 0.035 wt % of propyleneglycol, and 0.025 wt % of a 45 wt % aqueous solution of diethylenetriaminepentaacetic acid pentasodium as a chelating agent were added in a form of a mixture solution (so as to be contained in these amounts). Then, the resultant was mixed so that a water absorbent agent composition (22) was obtained.

The results of the deodorizing test A on the resulting water absorbent agent composition (22), a stabilization index, a degradable soluble component, and an AAP in the test on stability in maintaining a deodorizing effect of the resulting water absorbent agent composition (22), and the deodorizing test B on an absorbent article (22) are shown in Table 3.

Example 23

To the water absorbent resin particles (1) obtained in Production Example 1, 5.0 wt % of a green tea extract as a natural ingredient and 0.025 wt % of a 45 wt % aqueous solution of diethylenetriaminepentaacetic acid pentasodium as a chelating agent were added in a form of a mixture solution (so as to be contained in these amounts). Then, 100 ppm of propyl gallate as a temporal deterioration preventing agent was further mixed (dry-blended) with the resultant so that a water absorbent agent composition (23) was obtained. The green tea extract used was an aqueous solution obtained through the same operation as in Example 1.

The results of the deodorizing test A on the resulting water absorbent agent composition (23), a stabilization index, a degradable soluble component, and an AAP in the test on stability in maintaining a deodorizing effect of the resulting water absorbent agent composition (23), and the deodorizing test B on an absorbent article (23) are shown in Table 3.

TABLE 3

"Ex." stands for "Example".

| | Water absorbent resin particles | Natural ingredient Kind (extract) | Added amount [wt %] | Temporal deterioration preventing agent kind | Added amount [ppm] | Water [wt %] | Hydrophilic solvent [wt %] | Water absorbent agent composition | Physical properties of water absorbent agent composition | | | | Absorbent article Deodorizing test B |
|---|---|---|---|---|---|---|---|---|---|---|---|---|---|
| | | | | | | | | | Deodorizing test A | Stabilization index [%] | Degradable soluble component [wt %] | AAP [g/g] | |
| Ex. 1 | (1) | Green tea | 5.0 | propyl gallate | 100 | — | — | (1) | 2.5 | 100 | 18 | 26 | 2.9 |
| Ex. 11 | (1) | Theaceae plant leaves | 0.015 | propylparaben | 0.1 | 0.085 | — | (11) | 2.9 | 97 | 26 | 26 | 2.8 |
| Ex. 21 | (1) | Green tea | 5.0 | propyl gallate | 100 | — | 0.5 | (21) | 2.5 | 100 | 18 | 29 | 2.9 |
| Ex. 22 | (1) | Theaceae plant leaves | 0.015 | propylparaben | 0.1 | 0.085 | 0.035 | (22) | 2.8 | 100 | 26 | 29 | 2.8 |
| Ex. 23 | (1) | Green tea | 5.0 | propyl gallate (dry-blended) | 100 | — | — | (23) | 2.6 | 90 | 18 | 28 | 2.8 |

As is seen from Table 3, use of the hydrophilic organic solvent (polyol) in addition of the natural ingredient and/or the temporal deterioration preventing agent to the water absorbent resin allows a reduction in damage to powder, so that a reduction in AAP can be prevented. This shows that the water absorbent agent composition of the present invention preferably contains polyol.

Dry-blending the temporal deterioration preventing agent with the water absorbent resin separately from the natural ingredient results in a great decrease in deodorizing function with time. This shows that it is desirable to add a mixture of the natural ingredient and the temporal deterioration preventing agent (the natural ingredient and the temporal deterioration preventing agent simultaneously) to the water absorbent resin.

Example 24

To the water absorbent agent composition (5) obtained in Example 5, 0.5 wt % of Reolosil QS-20 (hydrophilic amorphous silica, manufactured by TOKUYAMA) serving as water-insoluble microparticles was mixed evenly, so that a water absorbent agent composition (24) was obtained.

The results of the deodorizing test A on the resulting water absorbent agent composition (24), a stabilization index, a degradable soluble component, and a moisture absorption blocking ratio (BR) in the test on stability in maintaining a deodorizing effect of the resulting water absorbent agent composition (24), and the deodorizing test B on an absorbent article (24) are shown in Table 4.

Example 25

To the water absorbent agent composition (21) obtained in Example 21, 0.15 wt % of Reolosil QS-20 (hydrophilic amorphous silica, manufactured by TOKUYAMA) serving as water-insoluble microparticles was mixed evenly, so that a water absorbent agent composition (25) was obtained.

The results of the deodorizing test A on the resulting water absorbent agent composition (25), a stabilization index, a degradable soluble component, and a moisture absorption blocking ratio (BR) in the test on stability in maintaining a deodorizing effect of the resulting water absorbent agent composition (25), and the deodorizing test B on an absorbent article (25) are shown in Table 4.

ity of the powder under high humidity, thereby improving handleability of the water absorbent agent composition.

Example 26

A water absorbent agent composition (26) was obtained by carrying out the same operation as in Example 1 except that the chelating agent was not added out of the natural ingredient, the temporal deterioration preventing agent, and the chelating agent.

The results of the deodorizing test A on the resulting water absorbent agent composition (26), a stabilization index and a degradable soluble component in the test on stability in maintaining a deodorizing effect of the resulting water absorbent agent composition (26), and the deodorizing test B on an absorbent article (26) are shown in Table 5.

Example 27

A water absorbent agent composition (27) was obtained by carrying out the same operation as in Example 11 except that the chelating agent was not added out of the natural ingredient, the temporal deterioration preventing agent, the chelating agent, and the water.

The results of the deodorizing test A on the resulting water absorbent agent composition (27), a stabilization index and a degradable soluble component in the test on stability in maintaining a deodorizing effect of the resulting water

TABLE 4

"Ex." stands for "Example".

| | Water absorbent resin particles | Natural ingredient Kind (extract) | Natural ingredient Added amount [wt %] | Temporal deterioration preventing agent kind | Temporal deterioration preventing agent Added amount [ppm] | Water [wt %] | Hydrophilic solvent [wt %] | Water insoluble microparticles [wt %] | Water absorbent agent composition | Physical properties of water absorbent agent composition Deodorizing test A | Physical properties of water absorbent agent composition Stabilization index [%] | Physical properties of water absorbent agent composition Degradable soluble component [wt %] | BR [wt %] | Absorbent article Deodorizing test B |
|---|---|---|---|---|---|---|---|---|---|---|---|---|---|---|
| Ex. 5 | (2) | Oolong tea | 3.0 | sodium erythorbate | 50 | 7.0 | — | — | (5) | 2.3 | 100 | 21 | 100 | 2.6 |
| Ex. 21 | (1) | Green tea | 5.0 | propyl gallate | 100 | — | 0.5 | — | (21) | 2.5 | 100 | 18 | 100 | 2.9 |
| Ex. 24 | (2) | Oolong tea | 3.0 | sodium erythorbate | 50 | 7.0 | — | 0.5 | (24) | 2.3 | 100 | 21 | 0 | 2.6 |
| Ex. 25 | (1) | Green tea | 5.0 | propyl gallate | 100 | — | 0.5 | 0.15 | (25) | 2.5 | 100 | 18 | 0 | 2.8 |

As is seen from Table 4, appropriate addition of water-insoluble microparticles allows an improvement in flowability of the powder under high humidity, thereby improving handleability of the water absorbent agent composition.

absorbent agent composition (27), and the deodorizing test B on an absorbent article (27) are shown in Table 5.

TABLE 5

"Ex." stands for "Example".

| | Water absorbent particles | Natural ingredient Kind (extract) | Natural ingredient Added amount [wt %] | Temporal deterioration preventing agent kind | Temporal deterioration preventing agent Added amount [ppm] | Water [wt %] | Chelating agent aqueous solution [wt %] | Water absorbent agent composition | Physical properties of water absorbent agent composition Deodorizing test A | Physical properties of water absorbent agent composition Stabilization index [%] | Physical properties of water absorbent agent composition Degradable soluble component [wt %] | Absorbent article Deodorizing test B |
|---|---|---|---|---|---|---|---|---|---|---|---|---|
| Ex. 1 | (1) | Green tea | 5.0 | propyl gallate | 100 | — | 0.025 | (1) | 2.5 | 100 | 18 | 2.9 |
| Ex. 11 | (1) | Theaceae plant leaves | 0.015 | propylparaben | 0.1 | 0.085 | 0.025 | (11) | 2.9 | 97 | 26 | 2.8 |
| Ex. 26 | (1) | Green tea | 5.0 | propyl gallate | 100 | — | — | (26) | 3.0 | 97 | 53 | 3.1 |

TABLE 5-continued

"Ex." stands for "Example".

| | Water absorbent particles | Natural ingredient Kind (extract) | Added amount [wt %] | Temporal deterioration preventing agent kind | Added amount [ppm] | Water [wt %] | Chelating agent aqueous solution [wt %] | Physical properties of water absorbent agent composition | | | | |
|---|---|---|---|---|---|---|---|---|---|---|---|---|
| | | | | | | | | Water absorbent agent composition | Deodorizing test A | Stabilization index [%] | Degradable soluble component [wt %] | Absorbent article Deodorizing test B |
| Ex. 27 | (1) | Theaceae plant leaves | 0.015 | propylparaben | 0.1 | 0.085 | — | (27) | 3.2 | 100 | 48 | 3.2 |

As is seen from Table 5, simultaneous addition of the natural ingredient (deodorizing ingredient in particular) and the temporal deterioration preventing agent and use of the chelating agent in combination allow a further improvement in deodorizing performance.

ticles (1) or (2), the amounts of Fe in the water absorbent agent compositions (1)-(27) were similar to the amount of Fe in the water absorbent resin particles (1) or (2).

TABLE 6

"Ex." stands for "Example".

| | Water absorbent resin particles | Natural ingredient Kind (extract) | Added amount [wt %] | Temporal deterioration preventing agent kind | Added amount [ppm] | Water [wt %] | Amount of Fe [ppm] | Water absorbent agent composition | Deodorizing test A | Stabilization index [%] | Degradable soluble component [wt %] | Absorbent article Deodorizing test B |
|---|---|---|---|---|---|---|---|---|---|---|---|---|
| Ex. 1 | (1) | Green tea | 5.0 | propyl gallate | 100 | — | 0.28 | (1) | 2.5 | 100 | 18 | 2.9 |
| Ex. 28 | (3) | Green tea | 5.0 | propyl gallate | 100 | — | 3.5 | (28) | 2.9 | 91 | 51 | 3.2 |

Production Example 3

Surface crosslinked water absorbent resin particles (3) were obtained by carrying out the same operation as in Production Example 1 except that the 48% aqueous solution of sodium hydrate containing 0.4 ppm of Fe, which had been used to obtain the sodium acrylate aqueous solution whose neutralization rate was 75 mol %, was replaced with a 48% aqueous solution of sodium hydrate containing 5 ppm of Fe.

Comparative Example 8

A water absorbent agent composition (28) was obtained by carrying out the same operation as in Example 1 except that the water absorbent resin particles (1) used in Example 1 were replaced with the water absorbent resin particles (3) obtained in Production Example 3.

Results of measurements of amount of Fe etc. in the resulting water absorbent agent composition (28) are shown in Table 6. The amount of Fe in the water absorbent agent composition (28) is mainly the amount of Fe in the water absorbent resin particles (3) which was derived from the 48% sodium hydrate aqueous solution used to obtain the sodium acrylate aqueous solution whose neutralization rate was 75 mol %.

Accordingly, also in cases of the water absorbent agent compositions (1)-(27) using the water absorbent resin par- As is seen from Table 6, reducing the amount of Fe results in a decrease in degradable soluble component. This shows that a smaller amount of Fe is more preferable from the viewpoint of not only the deodorizing function but also prevention of a deterioration of the water absorbent resin particles.

INDUSTRIAL APPLICABILITY

A water absorbent agent composition in accordance with the present invention is used as a member constituting an absorbent article. The water absorbent agent composition is used not only for sanitary materials such as an adult paper diaper, a child paper diaper, a sanitary napkin, and an incontinence pad but also for a water stop agent for engineering works and construction, a moisture absorbent, a dehumidifying agent, a water retention agent for agricultural gardening, and the like.

The invention claimed is:

1. A water absorbent agent composition comprising: a polycarboxylic acid (salt)-based water absorbent resin as a main component; a natural ingredient produced by a living organism; and a temporal deterioration preventing agent in an amount of 0.05 ppm to 120 ppm, wherein said temporal deterioration preventing agent is at least one of (a) a water-soluble reducing agent selected from the group consisting of erythorbic acid, L-ascorbic acid, and sulfites, (b) water-soluble oxidants selected from the group consisting of hypochlorous acids and hypochlorites, (c) phenylphenols, (d) benzoic acid or esters thereof, and (e) hydroxybenzoic acid or esters thereof, where the polycarboxylic acid (salt)- based water absorbent resin is a crosslinked polymer of unsaturated monomers, and the unsaturated monomers contain iron (Fe) in an amount of not more than 2 ppm based on the water absorbent agent composition.

2. The water absorbent agent composition as set forth in claim 1, wherein the natural ingredient is an extract of a plant selected from the group consisting of Theaceae, Rubiaceae, Gramineae, and Fagaceae; and
the temporal deterioration preventing agent is at least one kind of a synthetic ingredient selected from the group consisting of an antioxidant, a preservative, a germicide, an antibacterial agent, an antiseptic agent, and an antifungal agent.

3. The water absorbent agent composition as set forth in claim 1, wherein:
the natural ingredient is a plant ingredient containing caffeine or catechins, or a plant ingredient containing tannin;
(i) the water absorbent agent composition contains the natural ingredient in an amount of 0.01 to 15 wt % specified by a solid content excluding a solvent in a case where the natural ingredient is an extract, or (ii) the water absorbent agent composition contains caffeine and/or catechins in a total amount of 5 ppm to 1 wt %, or (iii) the water absorbent agent composition contains tannin in an amount of 5 ppm to 1 wt %; and
the water absorbent agent composition contains the temporal deterioration preventing agent in a weight ratio of 1/10 to 1/10000 specified by a solid content excluding a solvent in a case where the natural ingredient is an extract relative to the natural ingredient or the caffeine and/or the catechins, or the tannin.

4. The water absorbent agent composition as set forth in claim 1, wherein the water absorbent agent composition has a moisture content of 1 to 15 wt %.

5. The water absorbent agent composition as set forth in claim 1, wherein:
the polycarboxylic acid (salt)-based water absorbent resin is a polyacrylic acid (salt)-based water absorbent resin having a neutralization rate of 30 to 80 mol %;
the water absorbent agent composition is in the form of particulates; and
the water absorbent agent composition further satisfies at least one of physical properties specified by the following (1) through (4):
(1) having a degradable soluble component of not more than 40 wt %;
(2) containing particles having a particle diameter specified by a standard sieve of not less than 150 μm and less than 850 μm in an amount of not less than 90 wt % of the total water absorbent agent composition, and containing particles having a particle diameter specified by a standard sieve of not less than 300 μm in an amount of not less than 60 wt % of the total water absorbent agent composition;
(3) having a water absorption capacity under load (AAP) specified in ERT442.2-02 of not less than 15 [g/g]; and
(4) having a moisture absorption blocking rate of not more than 30 wt %.

6. The water absorbent agent composition as set forth in claim 1,
further comprising a chelating agent; or
further comprising water-insoluble microparticles; further comprising polyol.

7. A water absorbent agent package comprising a sealed container filled with a water absorbent agent composition recited in claim 1.

8. A storing or stocking method comprising storing a water absorbent agent package recited in claim 7 in a packaged state for not less than 30 days prior after packaging the water absorbent agent package.

9. A storing or stocking method comprising storing a packaged absorbent article for urine absorption in a packaged state for not less than 30 days after packaging the packaged absorbent article for urine absorption is used, the packaged absorbent article for urine absorption containing a water absorbent agent composition recited in claim 1.

10. A method for producing a water absorbent agent composition, comprising simultaneously or separately mixing a natural ingredient produced from a living organism and a temporal deterioration preventing agent with a polycarboxylic acid (salt)-based water absorbent resin which is a crosslinked polymer of unsaturated monomers having carboxylic acid and/or a salt thereof, and the unsaturated monomers contain iron (Fe) in an amount of not more than 2 ppm based on the water absorbent agent composition, and where the temporal deterioration preventing agent is mixed in an amount of 0.05 ppm to 120 ppm, wherein said temporal deterioration preventing agent is at least one of (a) a water-soluble reducing agent selected from the group consisting of erythorbic acid, L-ascorbic acid, and sulfites, (b) water-soluble oxidants selected from the group consisting of hypochlorous acids and hypochlorites, (c) phenylphenols, (d) benzoic acid or esters thereof, and (e) hydroxybenzoic acid or esters thereof.

11. The method as set forth in claim 10, wherein the natural ingredient is an extract of a plant selected from the group consisting of Theaceae, Rubiaceae, Gramineae, and Fagaceae; and
the temporal deterioration preventing agent is at least one kind of a synthetic ingredient selected from the group consisting of an antioxidant, a preservative, a germicide, an antibacterial agent, an antiseptic agent, and an antifungal agent.

12. The method as set forth in claim 10, wherein:
the natural ingredient and the temporal deterioration preventing agent are mixed with the water absorbent resin in respective amounts of 0.01 to 15 wt % and 0.05 to 120 ppm specified by a solid content excluding a solvent in a case where the natural ingredient is an extract; and
the water absorbent agent composition contains the temporal deterioration preventing agent in a weight ratio of 1/10 to 1/10000 specified by a solid content excluding a solvent in a case where the natural ingredient is an extract relative to the natural ingredient or the caffeine and/or the catechins, or the tannin.

13. The method as set forth in claim 10, wherein the water absorbent agent composition has a moisture content of 1 to 15 wt %.

14. An absorbent article production method comprising combining a crosslinked polycarboxylic acid(salt)-based water absorbent resin as a main component; a natural ingredient produced by a living organism agent, and a temporal deterioration preventing agent to obtain a water absorbent agent composition, and forming an absorbent article for urine absorption containing the water absorbent agent composition, where the polycarboxylic acid(salt)-based water absorbent resin is a crosslinked polymer of unsaturated monomers, and the unsaturated monomers contain iron (Fe) in an amount of not more than 2 ppm based on the water absorbent agent composition, and the temporal deterioration preventing agent is combined in an amount of 0.05 ppm to 120 ppm, wherein said temporal deterioration preventing agent is at least one of (a) a water-soluble reducing agent selected from the group consisting of erythorbic acid, L-ascorbic acid, and sulfites, (b) water-soluble oxidants selected from the group consisting of hypochlorous acids and hypochlorites, (c) phenylphenols, (d) benzoic acid or esters thereof, and (e) hydroxybenzoic acid or esters thereof.

* * * * *